(12) United States Patent
Kaiser et al.

(10) Patent No.: US 9,445,827 B2
(45) Date of Patent: Sep. 20, 2016

(54) METHOD AND APPARATUS FOR INTRAOSSEOUS MEMBRANE RECONSTRUCTION

(71) Applicant: Biomet Sports Medicine, LLC, Warsaw, IN (US)

(72) Inventors: Ryan A. Kaiser, Leesburg, IN (US); Kevin T. Stone, Winona Lake, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 537 days.

(21) Appl. No.: 13/964,558

(22) Filed: Aug. 12, 2013

(65) Prior Publication Data

US 2013/0331848 A1 Dec. 12, 2013

Related U.S. Application Data

(62) Division of application No. 13/281,016, filed on Oct. 25, 2011, now Pat. No. 8,506,597.

(51) Int. Cl.
*A61B 17/17* (2006.01)
*A61B 17/56* (2006.01)
(Continued)

(52) U.S. Cl.
CPC ....... *A61B 17/1717* (2013.01); *A61B 17/0401* (2013.01); *A61B 17/0469* (2013.01); *A61B 17/0487* (2013.01); *A61B 17/17* (2013.01); *A61B 17/1796* (2013.01); *A61B 17/56* (2013.01); *A61B 17/06004* (2013.01); *A61B 2017/0404* (2013.01); *A61B 2017/0409* (2013.01); *A61B 2017/0414* (2013.01); *A61B 2017/0417* (2013.01);
(Continued)

(58) Field of Classification Search
CPC .. A61B 17/17; A61B 17/1796; A61B 17/15; A61B 17/151; A61B 17/842; A61B 17/56; A61B 17/1775; A61B 17/1717; A61B 2017/564; A61B 2017/0409
See application file for complete search history.

(56) References Cited

U.S. PATENT DOCUMENTS

| 65,499 A | 6/1867 | Miller |
|---|---|---|
| 126,366 A | 4/1872 | Wills |

(Continued)

FOREIGN PATENT DOCUMENTS

| AU | 4957264 | 3/1966 |
|---|---|---|
| AU | 440266 | 10/1967 |

(Continued)

OTHER PUBLICATIONS

"JuggerKnot™ Soft Anchor: Arthroscopic and Mini-Open Rotator Cuff Repair Using JuggerKnot™ Soft Anchor—2.9mm with ALLthread™ Knotless Anchor Surgical Technique" brochure, Biomet® Sports Medicine. (2013) 16 pages.

(Continued)

*Primary Examiner* — Dianne Dornbusch
(74) *Attorney, Agent, or Firm* — Schwegman Lundberg & Woessner, P.A.

(57) ABSTRACT

A method for repairing a defect in an interosseous membrane located between a first bone and a second bone. The method includes: coupling a flexible member to the first bone and the second bone, the flexible member extending past a first area of the interosseous membrane between the first bone and the second bone; and orienting the flexible member such that the flexible member extends generally parallel to fibers of the first area of the interosseous membrane.

18 Claims, 8 Drawing Sheets

(51) Int. Cl.
   *A61B 17/04*      (2006.01)
   *A61B 17/06*      (2006.01)

(52) U.S. Cl.
   CPC .............. *A61B 2017/0496* (2013.01); *A61B 2017/06042* (2013.01); *A61B 2017/564* (2013.01)

(56) References Cited

U.S. PATENT DOCUMENTS

| | | | |
|---|---|---|---|
| 233,475 A | 10/1880 | Cook et al. | |
| 261,501 A | 7/1882 | Vandermark | |
| 268,407 A | 12/1882 | Hughes | |
| 330,087 A | 11/1885 | Binns | |
| 394,739 A | 12/1888 | Toulmin | |
| 401,677 A | 4/1889 | Autenrieth | |
| 417,805 A | 12/1889 | Beaman | |
| 487,304 A | 12/1892 | Todd | |
| 762,710 A | 6/1901 | Hall | |
| 837,767 A | 12/1906 | Aims | |
| 838,203 A | 12/1906 | Neil | |
| 1,059,631 A | 4/1913 | Popovics | |
| 1,131,155 A | 3/1915 | Murphy | |
| 1,153,450 A | 9/1915 | Schaff | |
| 1,346,940 A | 7/1920 | Collins | |
| 1,635,066 A | 7/1927 | Wells | |
| 1,950,799 A | 3/1934 | Jones | |
| 2,065,659 A | 12/1936 | Cullen | |
| 2,108,206 A | 2/1938 | Meeker | |
| 2,121,193 A | 6/1938 | Hanicke | |
| 2,242,003 A | 5/1941 | Lorenzo | |
| 2,267,925 A | 12/1941 | Johnston | |
| 2,302,986 A | 11/1942 | Vollrath | |
| 2,329,398 A | 9/1943 | Duffy | |
| 2,397,216 A | 3/1946 | Stellin | |
| RE22,857 E | 3/1947 | Ogburn | |
| 2,526,959 A | 10/1950 | Lorenzo | |
| 2,528,456 A | 10/1950 | Stevenson | |
| 2,531,734 A * | 11/1950 | Hopkins ............ | A61B 17/1703 606/97 |
| 2,562,419 A | 7/1951 | Ferris | |
| 2,581,564 A | 1/1952 | Villegas | |
| 2,600,395 A | 6/1952 | Domoj et al. | |
| 2,610,631 A | 9/1952 | Calicchio | |
| 2,665,597 A | 1/1954 | Hill | |
| 2,669,774 A | 2/1954 | Mitchell | |
| 2,698,986 A | 1/1955 | Brown | |
| 2,760,488 A | 8/1956 | Pierce | |
| 2,833,284 A | 5/1958 | Springer | |
| 2,846,712 A | 8/1958 | Markman | |
| 2,860,393 A | 11/1958 | Brock | |
| 2,880,728 A | 4/1959 | Rights | |
| 2,881,762 A | 4/1959 | Lowrie | |
| 2,883,096 A | 4/1959 | Dawson | |
| 2,913,042 A | 11/1959 | Taylor | |
| 3,000,009 A | 9/1961 | Selstad | |
| 3,003,155 A | 10/1961 | Mielzynski et al. | |
| 3,013,559 A | 12/1961 | Thomas | |
| 3,037,619 A | 6/1962 | Stevans | |
| 3,039,460 A | 6/1962 | Chandler | |
| 3,081,781 A | 3/1963 | Stermer | |
| 3,090,386 A | 5/1963 | Curtis | |
| 3,103,666 A | 9/1963 | Bone | |
| 3,123,077 A | 3/1964 | Alcamo | |
| 3,125,095 A | 3/1964 | Kaufman et al. | |
| 3,171,408 A * | 3/1965 | Childs .................... | A61B 17/17 609/96 |
| 3,209,422 A | 10/1965 | Dritz | |
| 3,234,938 A | 2/1966 | Robinson | |
| 3,240,379 A | 3/1966 | Bremer et al. | |
| 3,250,271 A | 5/1966 | Lippes | |
| 3,399,432 A | 9/1968 | Merser | |
| 3,409,014 A | 11/1968 | Shannon | |
| RE26,501 E | 12/1968 | Himmelstein et al. | |
| 3,435,475 A | 4/1969 | Bisk | |
| 3,467,089 A | 9/1969 | Hasson | |
| 3,470,834 A | 10/1969 | Bone | |
| 3,470,875 A | 10/1969 | Johnson | |
| 3,500,820 A | 3/1970 | Almen | |
| 3,507,274 A | 4/1970 | Soichet | |
| 3,513,484 A | 5/1970 | Hausner | |
| 3,515,132 A | 6/1970 | McKnight | |
| 3,522,803 A | 8/1970 | Majzlin | |
| 3,527,223 A | 9/1970 | Shein | |
| 3,533,406 A | 10/1970 | Hutterer et al. | |
| 3,541,591 A | 11/1970 | Hoegerman | |
| 3,547,389 A | 12/1970 | Mitchell | |
| 3,579,831 A | 5/1971 | Stevens et al. | |
| 3,590,616 A | 7/1971 | Schussler et al. | |
| 3,608,095 A | 9/1971 | Barry | |
| 3,618,447 A | 11/1971 | Goins | |
| 3,628,530 A | 12/1971 | Schwartz | |
| 3,643,649 A | 2/1972 | Amato | |
| 3,648,705 A | 3/1972 | Lary | |
| 3,656,483 A | 4/1972 | Rudel | |
| 3,659,597 A | 5/1972 | Wolfers | |
| 3,664,345 A | 5/1972 | Dabbs et al. | |
| 3,665,560 A | 5/1972 | Bennett et al. | |
| 3,675,639 A | 7/1972 | Cimber | |
| 3,683,422 A | 8/1972 | Stemmer et al. | |
| 3,692,022 A | 9/1972 | Ewing | |
| 3,695,271 A | 10/1972 | Chodorow | |
| 3,699,969 A | 10/1972 | Allen | |
| 3,716,058 A | 2/1973 | Tanner, Jr. | |
| 3,744,488 A | 7/1973 | Cox | |
| 3,752,516 A | 8/1973 | Mumma | |
| 3,757,629 A | 9/1973 | Schneider | |
| 3,763,856 A | 10/1973 | Blomberg | |
| 3,771,520 A | 11/1973 | Lerner | |
| 3,777,748 A | 12/1973 | Abramson | |
| 3,807,407 A | 4/1974 | Schweizer | |
| 3,810,456 A | 5/1974 | Karman | |
| 3,825,010 A | 7/1974 | McDonald | |
| 3,840,017 A | 10/1974 | Violante et al. | |
| 3,842,824 A | 10/1974 | Neufeld | |
| 3,842,840 A | 10/1974 | Schweizer | |
| 3,845,772 A | 11/1974 | Smith | |
| 3,867,933 A | 2/1975 | Kitrilakis | |
| 3,867,944 A | 2/1975 | Samuels | |
| 3,871,368 A | 3/1975 | Johnson et al. | |
| 3,871,379 A | 3/1975 | Clarke | |
| 3,874,388 A | 4/1975 | King et al. | |
| 3,875,648 A | 4/1975 | Bone | |
| 3,877,570 A | 4/1975 | Barry | |
| 3,880,156 A | 4/1975 | Hoff | |
| 3,881,475 A | 5/1975 | Gordon et al. | |
| 3,889,666 A | 6/1975 | Lerner | |
| 3,892,240 A | 7/1975 | Park | |
| 3,896,500 A | 7/1975 | Rambert et al. | |
| 3,907,442 A | 9/1975 | Reid | |
| 3,910,281 A | 10/1975 | Kletschka et al. | |
| 3,918,444 A | 11/1975 | Hoff et al. | |
| 3,918,455 A | 11/1975 | Coplan | |
| 3,927,666 A | 12/1975 | Hoff | |
| 3,931,667 A | 1/1976 | Merser et al. | |
| 3,933,153 A | 1/1976 | Csatary et al. | |
| 3,937,217 A | 2/1976 | Kosonen et al. | |
| 3,943,932 A | 3/1976 | Woo | |
| 3,946,446 A | 3/1976 | Schofield | |
| 3,946,728 A | 3/1976 | Bettex | |
| 3,946,740 A | 3/1976 | Bassett | |
| 3,953,896 A | 5/1976 | Treace | |
| 3,954,103 A | 5/1976 | Garcia-Roel et al. | |
| 3,961,632 A | 6/1976 | Moossun | |
| 3,973,560 A | 8/1976 | Emmett et al. | |
| 3,976,079 A | 8/1976 | Samuels et al. | |
| 3,977,050 A | 8/1976 | Perez et al. | |
| 3,979,799 A | 9/1976 | Merser et al. | |
| 3,985,138 A | 10/1976 | Jarvik | |
| 3,990,619 A | 11/1976 | Russell | |
| 4,005,707 A | 2/1977 | Moulding, Jr. | |
| 4,006,747 A | 2/1977 | Kronenthal et al. | |
| 4,007,743 A | 2/1977 | Blake | |
| 4,013,071 A | 3/1977 | Rosenberg et al. | |
| 4,026,281 A | 5/1977 | Mayberry et al. | |

(56) References Cited

U.S. PATENT DOCUMENTS

| | | | |
|---|---|---|---|
| 4,036,101 A | 7/1977 | Burnett | |
| 4,050,100 A | 9/1977 | Barry | |
| 4,054,954 A | 10/1977 | Nakayama et al. | |
| 4,084,478 A | 4/1978 | Simmons | |
| 4,085,466 A | 4/1978 | Goodfellow et al. | |
| 4,094,313 A | 6/1978 | Komamura et al. | |
| 4,099,750 A | 7/1978 | McGrew | |
| 4,103,690 A | 8/1978 | Harris | |
| RE29,819 E | 10/1978 | Bone | |
| 4,121,487 A | 10/1978 | Bone | |
| 4,143,656 A | 3/1979 | Holmes et al. | |
| 4,144,876 A | 3/1979 | DeLeo | |
| 4,146,022 A | 3/1979 | Johnson et al. | |
| 4,149,277 A | 4/1979 | Bokros | |
| 4,157,714 A | 6/1979 | Foltz et al. | |
| 4,158,250 A | 6/1979 | Ringwald | |
| 4,160,453 A | 7/1979 | Miller | |
| 4,164,225 A | 8/1979 | Johnson et al. | |
| 4,172,458 A | 10/1979 | Pereyra | |
| 4,175,555 A | 11/1979 | Herbert et al. | |
| 4,185,636 A | 1/1980 | Gabbay et al. | |
| 4,196,883 A | 4/1980 | Einhorn et al. | |
| 4,210,148 A | 7/1980 | Stivala | |
| 4,235,161 A | 11/1980 | Kunreuther | |
| 4,235,238 A | 11/1980 | Ogiu et al. | |
| 4,237,779 A | 12/1980 | Kunreuther | |
| 4,243,037 A | 1/1981 | Smith | |
| 4,249,525 A | 2/1981 | Krzeminski | |
| 4,263,913 A | 4/1981 | Malmin | |
| 4,265,246 A | 5/1981 | Barry | |
| 4,273,117 A | 6/1981 | Neuhauser et al. | |
| 4,275,490 A | 6/1981 | Bivins | |
| 4,275,717 A | 6/1981 | Bolesky | |
| 4,287,807 A | 9/1981 | Pacharis et al. | |
| 4,291,698 A | 9/1981 | Fuchs et al. | |
| 4,301,551 A | 11/1981 | Dore et al. | |
| 4,307,723 A | 12/1981 | Finney | |
| 4,312,337 A | 1/1982 | Donohue | |
| 4,316,469 A | 2/1982 | Kapitanov et al. | |
| 4,326,531 A | 4/1982 | Shimonaka et al. | |
| 4,345,601 A | 8/1982 | Fukuda | |
| 4,349,027 A | 9/1982 | DiFrancesco | |
| 4,383,527 A * | 5/1983 | Asnis | A61B 17/1721 606/96 |
| 4,388,921 A | 6/1983 | Sutter et al. | |
| 4,400,833 A | 8/1983 | Kurland | |
| 4,402,445 A | 9/1983 | Green | |
| 4,409,974 A | 10/1983 | Freedland | |
| 4,421,112 A * | 12/1983 | Mains | A61B 17/152 606/75 |
| 4,438,769 A | 3/1984 | Pratt et al. | |
| 4,441,489 A | 4/1984 | Evans et al. | |
| 4,450,835 A * | 5/1984 | Asnis | A61B 17/1721 606/65 |
| 4,454,875 A | 6/1984 | Pratt et al. | |
| 4,462,395 A | 7/1984 | Johnson | |
| 4,463,753 A | 8/1984 | Gustilo | |
| 4,473,102 A | 9/1984 | Ohman et al. | |
| 4,484,570 A | 11/1984 | Sutter et al. | |
| 4,489,446 A | 12/1984 | Reed | |
| 4,489,464 A | 12/1984 | Massari et al. | |
| 4,493,323 A | 1/1985 | Albright et al. | |
| 4,496,468 A | 1/1985 | House et al. | |
| 4,505,274 A | 3/1985 | Speelman | |
| 4,509,516 A | 4/1985 | Richmond | |
| 4,528,980 A * | 7/1985 | Kenna | A61B 17/1746 606/102 |
| 4,531,522 A | 7/1985 | Bedi et al. | |
| 4,532,926 A | 8/1985 | O'Holla | |
| 4,534,350 A | 8/1985 | Golden et al. | |
| 4,535,764 A | 8/1985 | Ebert | |
| 4,537,185 A | 8/1985 | Stednitz | |
| 4,549,545 A | 10/1985 | Levy | |
| 4,549,652 A | 10/1985 | Free | |
| 4,561,432 A | 12/1985 | Mazor | |
| 4,564,007 A | 1/1986 | Coombs et al. | |
| 4,570,623 A | 2/1986 | Ellison et al. | |
| 4,573,844 A | 3/1986 | Smith | |
| 4,576,608 A | 3/1986 | Homsy | |
| 4,584,722 A | 4/1986 | Levy et al. | |
| 4,587,963 A | 5/1986 | Leibinger et al. | |
| 4,590,928 A | 5/1986 | Hunt et al. | |
| 4,595,007 A | 6/1986 | Mericle | |
| 4,596,249 A | 6/1986 | Freda et al. | |
| 4,602,635 A | 7/1986 | Mulhollan et al. | |
| 4,602,636 A | 7/1986 | Noiles | |
| 4,604,997 A | 8/1986 | De Bastiani et al. | |
| 4,605,414 A | 8/1986 | Czajka | |
| 4,616,650 A | 10/1986 | Green et al. | |
| 4,621,640 A | 11/1986 | Mulhollan et al. | |
| 4,624,254 A | 11/1986 | McGarry et al. | |
| 4,632,100 A | 12/1986 | Somers et al. | |
| 4,635,637 A | 1/1987 | Schreiber | |
| 4,636,121 A | 1/1987 | Miller | |
| 4,641,652 A | 2/1987 | Hutterer et al. | |
| 4,649,916 A | 3/1987 | Frimberger | |
| 4,649,952 A | 3/1987 | Jobe | |
| 4,653,486 A | 3/1987 | Coker | |
| 4,653,487 A | 3/1987 | Maale | |
| 4,653,489 A | 3/1987 | Tronzo | |
| 4,655,777 A | 4/1987 | Dunn et al. | |
| 4,662,068 A | 5/1987 | Polonsky | |
| 4,667,662 A | 5/1987 | Titone et al. | |
| 4,667,675 A | 5/1987 | Davis | |
| 4,669,473 A | 6/1987 | Richards et al. | |
| 4,683,895 A | 8/1987 | Pohndorf | |
| 4,688,561 A | 8/1987 | Reese | |
| 4,690,169 A | 9/1987 | Jobe | |
| 4,696,300 A | 9/1987 | Anderson | |
| 4,705,040 A | 11/1987 | Mueller et al. | |
| 4,708,132 A | 11/1987 | Silvestrini | |
| 4,714,475 A | 12/1987 | Grundei et al. | |
| 4,716,893 A | 1/1988 | Fischer et al. | |
| 4,719,671 A | 1/1988 | Ito et al. | |
| 4,719,917 A | 1/1988 | Barrows et al. | |
| 4,723,540 A | 2/1988 | Gilmer, Jr. | |
| 4,724,839 A | 2/1988 | Bedi et al. | |
| 4,728,332 A | 3/1988 | Albrektsson | |
| 4,738,255 A | 4/1988 | Goble et al. | |
| 4,739,751 A | 4/1988 | Sapega et al. | |
| 4,741,330 A | 5/1988 | Hayhurst | |
| 4,741,336 A | 5/1988 | Failla et al. | |
| 4,744,353 A * | 5/1988 | McFarland | A61B 17/0401 606/96 |
| 4,744,793 A | 5/1988 | Parr et al. | |
| 4,750,492 A | 6/1988 | Jacobs | |
| 4,760,843 A | 8/1988 | Fischer et al. | |
| 4,760,844 A | 8/1988 | Kyle | |
| 4,760,848 A | 8/1988 | Hasson | |
| 4,770,663 A | 9/1988 | Hanslik et al. | |
| 4,772,261 A | 9/1988 | Von Hoff et al. | |
| 4,772,286 A | 9/1988 | Goble et al. | |
| 4,773,910 A | 9/1988 | Chen et al. | |
| 4,775,380 A | 10/1988 | Seedhom et al. | |
| 4,776,328 A | 10/1988 | Frey et al. | |
| 4,781,190 A | 11/1988 | Lee et al. | |
| 4,784,126 A | 11/1988 | Hourahane | |
| 4,787,882 A | 11/1988 | Claren et al. | |
| 4,790,297 A | 12/1988 | Luque et al. | |
| 4,793,363 A | 12/1988 | Ausherman et al. | |
| 4,809,695 A | 3/1989 | Gwathmey et al. | |
| 4,813,406 A | 3/1989 | Ogle, II | |
| 4,823,794 A | 4/1989 | Pierce | |
| 4,828,562 A | 5/1989 | Kenna | |
| 4,832,026 A | 5/1989 | Jones | |
| 4,834,098 A | 5/1989 | Jones | |
| 4,838,282 A | 6/1989 | Strasser et al. | |
| 4,841,960 A | 6/1989 | Garner | |
| 4,851,005 A | 7/1989 | Hunt et al. | |
| 4,858,608 A | 8/1989 | McQuilkin et al. | |
| 4,860,513 A | 8/1989 | Whitman | |
| 4,863,383 A | 9/1989 | Grafelmann et al. | |
| 4,870,957 A | 10/1989 | Goble et al. | |
| 4,873,976 A | 10/1989 | Schreiber | |

(56) References Cited

U.S. PATENT DOCUMENTS

| | | | |
|---|---|---|---|
| 4,887,601 A | 12/1989 | Richards | |
| 4,889,110 A * | 12/1989 | Galline | A61B 17/1795 |
| | | | 140/121 |
| 4,890,615 A | 1/1990 | Caspari et al. | |
| 4,893,619 A | 1/1990 | Dale et al. | |
| 4,893,974 A | 1/1990 | Fischer et al. | |
| 4,895,148 A | 1/1990 | Bays et al. | |
| 4,896,668 A | 1/1990 | Popoff et al. | |
| 4,898,156 A | 2/1990 | Gatturna et al. | |
| 4,899,743 A | 2/1990 | Nicholson et al. | |
| 4,901,721 A | 2/1990 | Hakki | |
| 4,911,153 A * | 3/1990 | Border | A61B 17/1725 |
| | | | 606/64 |
| 4,922,897 A | 5/1990 | Sapega et al. | |
| 4,923,461 A | 5/1990 | Caspari et al. | |
| 4,927,421 A | 5/1990 | Goble et al. | |
| 4,946,377 A | 8/1990 | Kovach | |
| 4,946,468 A | 8/1990 | Li | |
| 4,950,270 A | 8/1990 | Bowman et al. | |
| 4,950,285 A | 8/1990 | Wilk | |
| 4,960,381 A | 10/1990 | Niznick | |
| 4,961,741 A | 10/1990 | Hayhurst | |
| 4,968,315 A | 11/1990 | Gatturna | |
| 4,968,317 A | 11/1990 | Tormala et al. | |
| 4,969,886 A | 11/1990 | Cziffer et al. | |
| 4,974,488 A | 12/1990 | Spralja | |
| 4,976,736 A | 12/1990 | White et al. | |
| 4,978,350 A | 12/1990 | Wagenknecht et al. | |
| 4,979,956 A | 12/1990 | Silvestrini | |
| 4,983,176 A | 1/1991 | Cushman et al. | |
| 4,988,351 A | 1/1991 | Paulos et al. | |
| 4,994,074 A | 2/1991 | Bezwada et al. | |
| 4,997,433 A | 3/1991 | Goble et al. | |
| 5,002,550 A | 3/1991 | Li | |
| 5,002,562 A | 3/1991 | Oberlander | |
| 5,002,574 A | 3/1991 | May et al. | |
| 5,007,921 A | 4/1991 | Brown | |
| 5,030,224 A | 7/1991 | Wright et al. | |
| 5,030,235 A | 7/1991 | Campbell, Jr. | |
| 5,035,701 A | 7/1991 | Kabbara | |
| 5,037,422 A | 8/1991 | Hayhurst et al. | |
| 5,037,426 A | 8/1991 | Goble et al. | |
| 5,041,129 A | 8/1991 | Hayhurst et al. | |
| 5,046,513 A | 9/1991 | Gatturna et al. | |
| 5,047,030 A | 9/1991 | Draenert et al. | |
| 5,053,037 A * | 10/1991 | Lackey | A61B 17/155 |
| | | | 606/79 |
| 5,053,039 A * | 10/1991 | Hofmann | A61B 17/15 |
| | | | 606/86 R |
| 5,053,046 A | 10/1991 | Janese | |
| 5,053,047 A | 10/1991 | Yoon | |
| 5,059,201 A | 10/1991 | Asnis | |
| 5,059,206 A | 10/1991 | Winters | |
| 5,061,277 A | 10/1991 | Carpentier et al. | |
| 5,062,344 A | 11/1991 | Gerker | |
| 5,062,843 A | 11/1991 | Mahony, III | |
| 5,064,431 A | 11/1991 | Gilbertson et al. | |
| 5,071,420 A | 12/1991 | Paulos et al. | |
| 5,074,874 A | 12/1991 | Yoon et al. | |
| 5,078,719 A * | 1/1992 | Schreiber | A61B 17/152 |
| | | | 606/87 |
| 5,078,731 A | 1/1992 | Hayhurst | |
| 5,078,843 A | 1/1992 | Pratt | |
| 5,084,050 A | 1/1992 | Draenert | |
| 5,084,058 A | 1/1992 | Li | |
| 5,085,661 A | 2/1992 | Moss | |
| 5,087,263 A | 2/1992 | Li | |
| 5,087,309 A | 2/1992 | Melton, Jr. | |
| 5,089,012 A | 2/1992 | Prou | |
| 5,092,866 A | 3/1992 | Breard et al. | |
| 5,098,435 A | 3/1992 | Stednitz et al. | |
| 5,100,415 A | 3/1992 | Hayhurst | |
| 5,100,417 A | 3/1992 | Cerier et al. | |
| 5,108,433 A | 4/1992 | May et al. | |
| 5,116,337 A | 5/1992 | Johnson | |
| 5,116,373 A | 5/1992 | Jakob et al. | |
| 5,116,375 A | 5/1992 | Hofmann | |
| 5,122,144 A * | 6/1992 | Bert | A61B 17/154 |
| | | | 606/102 |
| 5,123,913 A | 6/1992 | Wilk et al. | |
| 5,123,914 A | 6/1992 | Cope | |
| 5,127,785 A | 7/1992 | Faucher et al. | |
| 5,129,901 A | 7/1992 | Decoste | |
| 5,129,902 A | 7/1992 | Goble et al. | |
| 5,129,904 A | 7/1992 | Illi et al. | |
| 5,129,906 A | 7/1992 | Ross et al. | |
| 5,129,909 A * | 7/1992 | Sutherland | A61B 17/155 |
| | | | 606/53 |
| 5,139,498 A | 8/1992 | Astudillo Ley | |
| 5,139,499 A | 8/1992 | Small et al. | |
| 5,139,520 A | 8/1992 | Rosenberg | |
| 5,143,498 A | 9/1992 | Whitman | |
| 5,147,362 A | 9/1992 | Goble | |
| 5,149,329 A | 9/1992 | Richardson | |
| 5,151,104 A | 9/1992 | Kenna | |
| 5,152,790 A | 10/1992 | Rosenberg et al. | |
| 5,154,189 A | 10/1992 | Oberlander | |
| 5,156,616 A | 10/1992 | Meadows et al. | |
| 5,163,960 A | 11/1992 | Bonutti | |
| D331,626 S | 12/1992 | Hayhurst et al. | |
| 5,169,400 A | 12/1992 | Muhling et al. | |
| 5,176,682 A | 1/1993 | Chow | |
| 5,178,629 A | 1/1993 | Kammerer | |
| 5,183,458 A | 2/1993 | Marx | |
| 5,190,545 A | 3/1993 | Corsi et al. | |
| 5,192,282 A | 3/1993 | Draenert et al. | |
| 5,197,987 A | 3/1993 | Koch et al. | |
| 5,199,135 A | 4/1993 | Gold | |
| 5,203,784 A | 4/1993 | Ross et al. | |
| 5,203,787 A | 4/1993 | Noblitt et al. | |
| 5,207,679 A | 5/1993 | Li | |
| 5,209,753 A | 5/1993 | Biedermann et al. | |
| 5,209,805 A | 5/1993 | Spraggins | |
| 5,211,647 A | 5/1993 | Schmieding | |
| 5,211,650 A | 5/1993 | Noda | |
| 5,214,987 A | 6/1993 | Fenton, Sr. | |
| 5,219,359 A | 6/1993 | McQuilkin et al. | |
| 5,222,976 A | 6/1993 | Yoon | |
| 5,224,946 A | 7/1993 | Hayhurst et al. | |
| 5,230,699 A | 7/1993 | Grasinger | |
| 5,232,436 A | 8/1993 | Janevski | |
| 5,234,435 A | 8/1993 | Seagrave, Jr. | |
| 5,235,238 A | 8/1993 | Nomura et al. | |
| 5,236,445 A | 8/1993 | Hayhurst et al. | |
| 5,236,461 A | 8/1993 | Forte | |
| 5,242,447 A | 9/1993 | Borzone | |
| 5,246,441 A | 9/1993 | Ross et al. | |
| 5,246,444 A * | 9/1993 | Schreiber | A61B 17/152 |
| | | | 606/87 |
| 5,249,899 A | 10/1993 | Wilson | |
| 5,250,053 A | 10/1993 | Snyder | |
| 5,254,119 A * | 10/1993 | Schreiber | A61B 17/152 |
| | | | 606/87 |
| 5,258,015 A | 11/1993 | Li et al. | |
| 5,258,016 A | 11/1993 | DiPoto et al. | |
| 5,258,040 A | 11/1993 | Bruchman et al. | |
| 5,261,908 A | 11/1993 | Campbell, Jr. | |
| 5,268,001 A | 12/1993 | Nicholson et al. | |
| 5,269,160 A | 12/1993 | Wood | |
| 5,269,783 A | 12/1993 | Sander | |
| 5,269,806 A | 12/1993 | Sardelis et al. | |
| 5,269,809 A | 12/1993 | Hayhurst et al. | |
| 5,279,311 A | 1/1994 | Snyder | |
| 5,281,422 A | 1/1994 | Badylak et al. | |
| 5,282,809 A | 2/1994 | Kammerer et al. | |
| 5,282,832 A | 2/1994 | Toso et al. | |
| 5,282,867 A | 2/1994 | Mikhail | |
| 5,285,040 A | 2/1994 | Brandberg et al. | |
| 5,290,217 A | 3/1994 | Campos | |
| 5,290,243 A | 3/1994 | Chodorow et al. | |
| 5,300,077 A * | 4/1994 | Howell | A61B 17/1714 |
| | | | 606/79 |
| 5,306,278 A * | 4/1994 | Dahl | A61B 17/17 |
| | | | 408/241 G |

(56) References Cited

U.S. PATENT DOCUMENTS

| | | |
|---|---|---|
| 5,306,301 A | 4/1994 | Graf et al. |
| 5,312,410 A | 5/1994 | Miller et al. |
| 5,312,422 A | 5/1994 | Trott |
| 5,312,438 A | 5/1994 | Johnson |
| 5,314,429 A | 5/1994 | Goble |
| 5,318,566 A | 6/1994 | Miller |
| 5,318,575 A | 6/1994 | Chesterfield et al. |
| 5,318,577 A | 6/1994 | Li |
| 5,318,578 A | 6/1994 | Hasson |
| 5,320,115 A | 6/1994 | Kenna |
| 5,320,626 A | 6/1994 | Schmieding |
| 5,320,633 A | 6/1994 | Allen et al. |
| 5,324,295 A * | 6/1994 | Shapiro .............. A61B 17/1714 606/86 R |
| 5,324,308 A | 6/1994 | Pierce |
| 5,330,489 A | 7/1994 | Green et al. |
| 5,333,625 A | 8/1994 | Klein |
| 5,334,204 A | 8/1994 | Clewett et al. |
| 5,336,229 A | 8/1994 | Noda |
| 5,336,231 A | 8/1994 | Adair |
| 5,336,240 A | 8/1994 | Metzler et al. |
| 5,339,870 A | 8/1994 | Green et al. |
| 5,342,369 A | 8/1994 | Harryman, II |
| 5,346,462 A | 9/1994 | Barber |
| 5,350,380 A | 9/1994 | Goble et al. |
| RE34,762 E | 10/1994 | Goble et al. |
| 5,354,292 A | 10/1994 | Braeuer et al. |
| 5,354,298 A | 10/1994 | Lee et al. |
| 5,356,412 A | 10/1994 | Golds et al. |
| 5,356,413 A | 10/1994 | Martins et al. |
| 5,356,417 A | 10/1994 | Golds |
| 5,358,511 A | 10/1994 | Gatturna et al. |
| 5,360,431 A | 11/1994 | Puno et al. |
| 5,362,294 A | 11/1994 | Seitzinger |
| 5,364,400 A | 11/1994 | Rego, Jr. et al. |
| 5,366,461 A | 11/1994 | Blasnik |
| 5,368,599 A | 11/1994 | Hirsch et al. |
| 5,370,661 A | 12/1994 | Branch |
| 5,370,662 A | 12/1994 | Stone et al. |
| 5,372,146 A | 12/1994 | Branch |
| 5,372,604 A | 12/1994 | Trott |
| 5,372,821 A | 12/1994 | Badylak et al. |
| 5,374,268 A | 12/1994 | Sander |
| 5,374,269 A | 12/1994 | Rosenberg |
| 5,379,492 A | 1/1995 | Glesser |
| 5,383,878 A | 1/1995 | Roger et al. |
| 5,383,904 A | 1/1995 | Totakura et al. |
| 5,385,567 A | 1/1995 | Goble |
| 5,391,171 A | 2/1995 | Schmieding |
| 5,391,176 A | 2/1995 | de la Torre |
| 5,391,182 A | 2/1995 | Chin |
| 5,393,302 A | 2/1995 | Clark et al. |
| RE34,871 E | 3/1995 | McGuire et al. |
| 5,395,374 A | 3/1995 | Miller et al. |
| 5,397,356 A | 3/1995 | Goble et al. |
| 5,403,328 A | 4/1995 | Shallman |
| 5,403,329 A | 4/1995 | Hinchcliffe |
| 5,403,348 A | 4/1995 | Bonutti |
| 5,405,359 A | 4/1995 | Pierce |
| 5,411,550 A | 5/1995 | Herweck et al. |
| 5,415,658 A | 5/1995 | Kilpela et al. |
| 5,417,690 A | 5/1995 | Sennett et al. |
| 5,417,691 A | 5/1995 | Hayhurst |
| 5,417,694 A * | 5/1995 | Marik .................. A61B 17/155 606/88 |
| 5,417,698 A | 5/1995 | Green et al. |
| 5,417,712 A | 5/1995 | Whittaker et al. |
| 5,423,819 A | 6/1995 | Small et al. |
| 5,423,821 A | 6/1995 | Pasque |
| 5,423,823 A | 6/1995 | Schmieding |
| 5,423,860 A | 6/1995 | Lizardi et al. |
| 5,425,733 A | 6/1995 | Schmieding |
| 5,425,766 A | 6/1995 | Bowald et al. |
| 5,433,751 A | 7/1995 | Christel et al. |
| 5,437,680 A | 8/1995 | Yoon |
| 5,437,685 A | 8/1995 | Blasnik |
| 5,439,684 A | 8/1995 | Prewett et al. |
| 5,441,508 A | 8/1995 | Gazielly et al. |
| 5,443,468 A | 8/1995 | Johnson |
| 5,443,482 A | 8/1995 | Stone et al. |
| 5,443,483 A | 8/1995 | Kirsch et al. |
| 5,443,509 A | 8/1995 | Boucher et al. |
| 5,445,833 A | 8/1995 | Badylak et al. |
| 5,447,512 A | 9/1995 | Wilson et al. |
| 5,449,361 A | 9/1995 | Preissman |
| 5,451,203 A | 9/1995 | Lamb |
| 5,454,811 A | 10/1995 | Huebner |
| 5,454,821 A | 10/1995 | Harm et al. |
| 5,456,685 A | 10/1995 | Huebner |
| 5,456,722 A | 10/1995 | McLeod et al. |
| 5,458,601 A | 10/1995 | Young, Jr. et al. |
| 5,458,604 A | 10/1995 | Schmieding |
| 5,462,542 A | 10/1995 | Alesi, Jr. |
| 5,462,560 A | 10/1995 | Stevens |
| 5,464,426 A | 11/1995 | Bonutti |
| 5,464,427 A | 11/1995 | Curtis et al. |
| 5,464,440 A | 11/1995 | Johansson et al. |
| 5,466,237 A | 11/1995 | Byrd, III et al. |
| 5,467,786 A | 11/1995 | Allen et al. |
| 5,470,334 A | 11/1995 | Ross et al. |
| 5,470,337 A | 11/1995 | Moss |
| 5,470,338 A | 11/1995 | Whitfield et al. |
| 5,472,452 A | 12/1995 | Trott |
| 5,474,565 A | 12/1995 | Trott |
| 5,474,568 A | 12/1995 | Scott |
| 5,474,572 A | 12/1995 | Hayhurst |
| 5,476,465 A | 12/1995 | Preissman |
| 5,478,344 A | 12/1995 | Stone et al. |
| 5,478,345 A | 12/1995 | Stone et al. |
| 5,480,403 A | 1/1996 | Lee et al. |
| 5,480,406 A | 1/1996 | Nolan et al. |
| 5,484,442 A | 1/1996 | Melker et al. |
| 5,486,197 A | 1/1996 | Le et al. |
| 5,490,750 A | 2/1996 | Gundy |
| 5,496,331 A | 3/1996 | Xu et al. |
| 5,496,348 A | 3/1996 | Bonutti |
| 5,500,000 A | 3/1996 | Feagin et al. |
| 5,505,735 A | 4/1996 | Li |
| 5,505,736 A | 4/1996 | Reimels et al. |
| 5,507,754 A | 4/1996 | Green et al. |
| 5,520,691 A | 5/1996 | Branch |
| 5,520,694 A | 5/1996 | Dance et al. |
| 5,520,700 A | 5/1996 | Beyar et al. |
| 5,520,702 A | 5/1996 | Sauer et al. |
| 5,522,817 A | 6/1996 | Sander et al. |
| 5,522,820 A | 6/1996 | Caspari et al. |
| 5,522,843 A | 6/1996 | Zang |
| 5,522,844 A | 6/1996 | Johnson |
| 5,522,845 A | 6/1996 | Wenstrom, Jr. |
| 5,522,846 A | 6/1996 | Bonutti |
| 5,524,946 A | 6/1996 | Thompson |
| 5,527,321 A | 6/1996 | Hinchliffe |
| 5,527,342 A | 6/1996 | Pietrzak et al. |
| 5,527,343 A | 6/1996 | Bonutti |
| 5,531,759 A | 7/1996 | Kensey et al. |
| 5,534,012 A | 7/1996 | Bonutti |
| 5,536,270 A | 7/1996 | Songer et al. |
| 5,540,698 A | 7/1996 | Preissman |
| 5,540,703 A | 7/1996 | Barker, Jr. et al. |
| 5,540,718 A | 7/1996 | Bartlett |
| 5,545,168 A | 8/1996 | Burke |
| 5,545,178 A | 8/1996 | Kensey et al. |
| 5,545,180 A | 8/1996 | Le et al. |
| 5,545,228 A | 8/1996 | Kambin |
| 5,549,613 A | 8/1996 | Goble et al. |
| 5,549,617 A | 8/1996 | Green et al. |
| 5,549,619 A | 8/1996 | Peters et al. |
| 5,549,630 A | 8/1996 | Bonutti |
| 5,549,631 A | 8/1996 | Bonutti |
| 5,562,668 A | 10/1996 | Johnson |
| 5,562,669 A | 10/1996 | McGuire |
| 5,562,683 A | 10/1996 | Chan |
| 5,562,685 A | 10/1996 | Mollenauer et al. |
| 5,562,686 A | 10/1996 | Sauer et al. |

(56) References Cited

U.S. PATENT DOCUMENTS

| | | |
|---|---|---|
| 5,569,269 A | 10/1996 | Hart et al. |
| 5,569,305 A | 10/1996 | Bonutti |
| 5,570,706 A | 11/1996 | Howell |
| 5,571,090 A | 11/1996 | Sherts |
| 5,571,104 A | 11/1996 | Li |
| 5,571,139 A | 11/1996 | Jenkins, Jr. |
| 5,572,655 A | 11/1996 | Tuljapurkar et al. |
| 5,573,286 A | 11/1996 | Rogozinski |
| 5,573,542 A | 11/1996 | Stevens |
| 5,573,548 A | 11/1996 | Nazre et al. |
| 5,577,299 A | 11/1996 | Thompson et al. |
| 5,578,057 A | 11/1996 | Wenstrom, Jr. |
| 5,584,695 A | 12/1996 | Lal Sachdeva et al. |
| 5,584,835 A | 12/1996 | Greenfield |
| 5,584,836 A | 12/1996 | Ballintyn et al. |
| 5,584,862 A | 12/1996 | Bonutti |
| 5,586,986 A | 12/1996 | Hinchliffe |
| 5,588,575 A | 12/1996 | Davignon |
| 5,591,180 A | 1/1997 | Hinchliffe |
| 5,591,181 A | 1/1997 | Stone et al. |
| 5,591,207 A | 1/1997 | Coleman |
| 5,593,407 A | 1/1997 | Reis |
| 5,593,425 A | 1/1997 | Bonutti et al. |
| 5,601,557 A | 2/1997 | Hayhurst |
| 5,601,559 A | 2/1997 | Melker et al. |
| 5,601,571 A | 2/1997 | Moss |
| 5,603,716 A | 2/1997 | Morgan et al. |
| 5,607,429 A | 3/1997 | Hayano et al. |
| 5,607,430 A | 3/1997 | Bailey |
| 5,613,971 A | 3/1997 | Lower et al. |
| 5,618,290 A | 4/1997 | Toy et al. |
| 5,626,611 A | 5/1997 | Liu et al. |
| 5,626,614 A | 5/1997 | Hart |
| 5,628,756 A | 5/1997 | Barker, Jr. et al. |
| 5,628,766 A | 5/1997 | Johnson |
| 5,630,824 A | 5/1997 | Hart |
| 5,632,748 A | 5/1997 | Beck, Jr. et al. |
| 5,641,256 A | 6/1997 | Gundy |
| 5,643,266 A | 7/1997 | Li |
| 5,643,269 A | 7/1997 | Harle et al. |
| 5,643,273 A | 7/1997 | Clark |
| 5,643,295 A | 7/1997 | Yoon |
| 5,643,319 A | 7/1997 | Green et al. |
| 5,643,320 A | 7/1997 | Lower et al. |
| 5,643,321 A | 7/1997 | McDevitt |
| 5,645,546 A | 7/1997 | Fard |
| 5,645,547 A | 7/1997 | Coleman |
| 5,645,568 A | 7/1997 | Chervitz et al. |
| 5,645,588 A | 7/1997 | Graf et al. |
| 5,647,874 A | 7/1997 | Hayhurst |
| 5,649,959 A | 7/1997 | Hannam et al. |
| 5,649,963 A | 7/1997 | McDevitt |
| 5,658,289 A | 8/1997 | Boucher et al. |
| 5,658,299 A | 8/1997 | Hart |
| 5,658,313 A | 8/1997 | Thal |
| 5,662,658 A | 9/1997 | Wenstrom, Jr. |
| 5,662,663 A | 9/1997 | Shallman |
| 5,662,681 A | 9/1997 | Nash et al. |
| 5,665,112 A | 9/1997 | Thal |
| 5,667,513 A | 9/1997 | Torrie et al. |
| 5,671,695 A | 9/1997 | Schroeder |
| 5,674,224 A | 10/1997 | Howell et al. |
| 5,679,723 A | 10/1997 | Cooper et al. |
| 5,681,334 A | 10/1997 | Evans et al. |
| 5,681,352 A | 10/1997 | Clancy, III et al. |
| 5,683,404 A | 11/1997 | Johnson |
| 5,683,419 A | 11/1997 | Thal |
| 5,688,284 A | 11/1997 | Chervitz et al. |
| 5,688,285 A | 11/1997 | Yamada et al. |
| 5,690,655 A | 11/1997 | Hart et al. |
| 5,690,676 A | 11/1997 | DiPoto et al. |
| 5,690,678 A | 11/1997 | Johnson |
| 5,693,046 A | 12/1997 | Songer et al. |
| 5,695,497 A | 12/1997 | Stahelin et al. |
| 5,697,929 A | 12/1997 | Mellinger |
| 5,697,933 A * | 12/1997 | Gundlapalli ....... A61B 17/1714 606/206 |
| 5,699,657 A | 12/1997 | Paulson |
| 5,702,397 A | 12/1997 | Goble et al. |
| 5,702,422 A | 12/1997 | Stone |
| 5,702,462 A | 12/1997 | Oberlander |
| 5,707,373 A | 1/1998 | Sevrain et al. |
| 5,709,708 A | 1/1998 | Thal |
| 5,711,969 A | 1/1998 | Patel et al. |
| 5,713,005 A | 1/1998 | Proebsting |
| 5,713,897 A | 2/1998 | Goble et al. |
| 5,713,904 A | 2/1998 | Errico et al. |
| 5,713,905 A | 2/1998 | Goble et al. |
| 5,713,921 A | 2/1998 | Bonutti |
| 5,715,578 A | 2/1998 | Knudson |
| 5,716,359 A | 2/1998 | Ojima et al. |
| 5,716,397 A | 2/1998 | Myers |
| 5,718,717 A | 2/1998 | Bonutti |
| 5,720,747 A | 2/1998 | Burke |
| 5,720,765 A | 2/1998 | Thal |
| 5,720,766 A | 2/1998 | Zang et al. |
| 5,722,976 A | 3/1998 | Brown |
| 5,725,529 A | 3/1998 | Nicholson et al. |
| 5,725,549 A | 3/1998 | Lam |
| 5,725,556 A | 3/1998 | Moser et al. |
| 5,725,581 A | 3/1998 | Branemark |
| 5,725,582 A | 3/1998 | Bevan et al. |
| 5,726,722 A | 3/1998 | Uehara et al. |
| 5,728,107 A | 3/1998 | Zlock et al. |
| 5,728,109 A | 3/1998 | Schulze et al. |
| 5,728,136 A | 3/1998 | Thal |
| 5,733,293 A | 3/1998 | Scirica et al. |
| 5,733,306 A | 3/1998 | Bonutti |
| 5,733,307 A | 3/1998 | Dinsdale |
| 5,735,875 A | 4/1998 | Bonutti et al. |
| 5,741,259 A | 4/1998 | Chan |
| 5,741,260 A | 4/1998 | Songer et al. |
| 5,741,281 A | 4/1998 | Martin et al. |
| 5,743,912 A | 4/1998 | Lahille et al. |
| 5,746,751 A | 5/1998 | Sherts |
| 5,746,752 A | 5/1998 | Burkhart |
| 5,746,754 A | 5/1998 | Chan |
| 5,749,898 A | 5/1998 | Schulze et al. |
| 5,755,729 A | 5/1998 | de la Torre et al. |
| 5,755,791 A | 5/1998 | Whitson et al. |
| 5,766,176 A | 6/1998 | Duncan |
| 5,766,218 A | 6/1998 | Arnott |
| 5,766,250 A | 6/1998 | Chervitz et al. |
| 5,769,894 A | 6/1998 | Ferragamo |
| 5,769,899 A | 6/1998 | Schwartz et al. |
| 5,772,673 A | 6/1998 | Cuny et al. |
| 5,776,196 A | 7/1998 | Matsuzaki et al. |
| 5,782,845 A | 7/1998 | Shewchuk |
| 5,782,862 A | 7/1998 | Bonutti |
| 5,782,864 A | 7/1998 | Lizardi |
| 5,782,866 A | 7/1998 | Wenstrom, Jr. |
| 5,785,714 A | 7/1998 | Morgan et al. |
| 5,792,142 A | 8/1998 | Galitzer |
| 5,792,149 A | 8/1998 | Sherts et al. |
| 5,796,127 A | 8/1998 | Hayafuji et al. |
| 5,797,913 A | 8/1998 | Dambreville et al. |
| 5,797,915 A | 8/1998 | Pierson, III et al. |
| 5,797,916 A | 8/1998 | McDowell |
| 5,797,928 A | 8/1998 | Kogasaka |
| 5,800,407 A | 9/1998 | Eldor et al. |
| 5,810,824 A | 9/1998 | Chan |
| 5,810,848 A | 9/1998 | Hayhurst |
| 5,814,056 A | 9/1998 | Prosst et al. |
| 5,814,069 A | 9/1998 | Schulze et al. |
| 5,814,070 A | 9/1998 | Borzone et al. |
| 5,814,072 A | 9/1998 | Bonutti |
| 5,814,073 A | 9/1998 | Bonutti |
| 5,823,980 A | 10/1998 | Kopfer |
| 5,824,011 A | 10/1998 | Stone et al. |
| 5,824,066 A | 10/1998 | Gross |
| 5,830,234 A | 11/1998 | Wojciechowicz et al. |
| 5,843,084 A | 12/1998 | Hart et al. |
| 5,845,645 A | 12/1998 | Bonutti |
| 5,846,254 A | 12/1998 | Schulze et al. |

(56) References Cited

U.S. PATENT DOCUMENTS

| | | | |
|---|---|---|---|
| 5,848,983 A | 12/1998 | Basaj et al. |
| 5,849,012 A | 12/1998 | Abboudi |
| 5,860,973 A | 1/1999 | Michelson |
| 5,860,978 A | 1/1999 | McDevitt et al. |
| 5,868,740 A | 2/1999 | LeVeen et al. |
| 5,868,748 A | 2/1999 | Burke |
| 5,868,789 A | 2/1999 | Huebner |
| 5,871,484 A | 2/1999 | Spievack et al. |
| 5,871,486 A | 2/1999 | Huebner et al. |
| 5,871,490 A | 2/1999 | Schulze et al. |
| 5,885,294 A | 3/1999 | Pedlick et al. |
| 5,891,168 A | 4/1999 | Thal |
| 5,893,592 A | 4/1999 | Schulze et al. |
| 5,895,395 A | 4/1999 | Yeung |
| 5,897,564 A | 4/1999 | Schulze et al. |
| 5,897,574 A | 4/1999 | Bonutti |
| 5,899,902 A | 5/1999 | Brown et al. |
| 5,899,938 A | 5/1999 | Sklar et al. |
| 5,908,421 A | 6/1999 | Beger et al. |
| 5,908,436 A | 6/1999 | Cuschieri et al. |
| 5,910,148 A | 6/1999 | Reimels et al. |
| 5,911,721 A | 6/1999 | Nicholson et al. |
| 5,918,604 A | 7/1999 | Whelan |
| 5,921,986 A | 7/1999 | Bonutti |
| 5,925,008 A | 7/1999 | Douglas |
| 5,928,231 A | 7/1999 | Klein et al. |
| 5,928,267 A | 7/1999 | Bonutti et al. |
| RE36,289 E | 8/1999 | Le et al. |
| 5,931,838 A | 8/1999 | Vito |
| 5,931,844 A | 8/1999 | Thompson et al. |
| 5,931,869 A | 8/1999 | Boucher et al. |
| 5,935,119 A | 8/1999 | Guy et al. |
| 5,935,133 A | 8/1999 | Wagner et al. |
| 5,935,149 A | 8/1999 | Ek |
| 5,938,668 A | 8/1999 | Scirica et al. |
| 5,941,439 A | 8/1999 | Kammerer et al. |
| 5,941,900 A | 8/1999 | Bonutti |
| 5,944,739 A | 8/1999 | Zlock et al. |
| 5,946,783 A | 9/1999 | Plociennik et al. |
| 5,947,915 A | 9/1999 | Thibodo, Jr. |
| 5,947,982 A | 9/1999 | Duran |
| 5,947,999 A | 9/1999 | Groiso |
| 5,948,002 A | 9/1999 | Bonutti |
| 5,951,559 A | 9/1999 | Burkhart |
| 5,951,560 A | 9/1999 | Simon et al. |
| 5,954,747 A | 9/1999 | Clark |
| 5,957,953 A | 9/1999 | DiPoto et al. |
| 5,961,520 A | 10/1999 | Beck, Jr. et al. |
| 5,961,521 A | 10/1999 | Roger et al. |
| 5,961,524 A | 10/1999 | Crombie |
| 5,964,764 A | 10/1999 | West, Jr. et al. |
| 5,964,767 A | 10/1999 | Tapia et al. |
| 5,964,769 A | 10/1999 | Wagner et al. |
| 5,964,783 A | 10/1999 | Grafton et al. |
| 5,968,045 A | 10/1999 | Frazier |
| 5,968,047 A | 10/1999 | Reed |
| 5,968,077 A | 10/1999 | Wojciechowicz et al. |
| 5,970,697 A | 10/1999 | Jacobs et al. |
| 5,972,006 A | 10/1999 | Sciaino, Jr. |
| 5,976,125 A | 11/1999 | Graham |
| 5,976,127 A | 11/1999 | Lax |
| 5,980,473 A | 11/1999 | Korakianitis et al. |
| 5,980,524 A | 11/1999 | Justin et al. |
| 5,980,539 A | 11/1999 | Kontos |
| 5,980,558 A | 11/1999 | Wiley |
| 5,980,559 A | 11/1999 | Bonutti |
| 5,989,252 A | 11/1999 | Fumex |
| 5,989,256 A | 11/1999 | Kuslich et al. |
| 5,989,282 A | 11/1999 | Bonutti |
| 5,993,452 A | 11/1999 | Vandewalle |
| 5,993,476 A | 11/1999 | Groiso |
| 5,997,542 A | 12/1999 | Burke |
| 5,997,552 A | 12/1999 | Person et al. |
| 5,997,575 A | 12/1999 | Whitson et al. |
| 6,001,100 A | 12/1999 | Sherman et al. |
| 6,001,106 A | 12/1999 | Ryan et al. |
| 6,007,538 A | 12/1999 | Levin |
| 6,007,567 A | 12/1999 | Bonutti |
| 6,010,525 A | 1/2000 | Bonutti et al. |
| 6,016,727 A | 1/2000 | Morgan |
| 6,019,767 A | 2/2000 | Howell |
| 6,022,352 A | 2/2000 | Vandewalle |
| 6,022,373 A | 2/2000 | Li |
| 6,024,758 A | 2/2000 | Thal |
| 6,027,523 A | 2/2000 | Schmieding |
| 6,030,410 A | 2/2000 | Zurbrugg |
| 6,033,429 A | 3/2000 | Magovern |
| 6,033,430 A | 3/2000 | Bonutti |
| 6,039,753 A | 3/2000 | Meislin |
| 6,041,485 A | 3/2000 | Pedlick et al. |
| 6,042,601 A | 3/2000 | Smith |
| 6,045,551 A | 4/2000 | Bonutti |
| 6,045,571 A | 4/2000 | Hill et al. |
| 6,045,572 A | 4/2000 | Johnson et al. |
| 6,045,573 A | 4/2000 | Wenstrom, Jr. et al. |
| 6,045,574 A | 4/2000 | Thal |
| 6,047,826 A | 4/2000 | Kalinski et al. |
| 6,048,343 A | 4/2000 | Mathis et al. |
| 6,051,006 A | 4/2000 | Shluzas et al. |
| 6,051,007 A | 4/2000 | Hogendijk et al. |
| 6,053,916 A | 4/2000 | Moore |
| 6,053,921 A | 4/2000 | Wagner et al. |
| 6,056,752 A | 5/2000 | Roger |
| 6,056,772 A | 5/2000 | Bonutti |
| 6,056,773 A | 5/2000 | Bonutti |
| 6,059,789 A * | 5/2000 | Dinger ............... A61B 17/1796 606/80 |
| 6,059,817 A | 5/2000 | Bonutti et al. |
| 6,059,818 A | 5/2000 | Johnson et al. |
| 6,062,344 A | 5/2000 | Okabe et al. |
| 6,066,173 A | 5/2000 | McKernan et al. |
| 6,068,648 A | 5/2000 | Cole et al. |
| 6,071,305 A | 6/2000 | Brown et al. |
| 6,074,403 A | 6/2000 | Nord |
| 6,077,277 A | 6/2000 | Mollenauer et al. |
| 6,077,292 A | 6/2000 | Bonutti |
| 6,080,185 A | 6/2000 | Johnson et al. |
| 6,086,591 A | 7/2000 | Bojarski |
| 6,086,592 A | 7/2000 | Rosenberg et al. |
| 6,086,608 A | 7/2000 | Ek et al. |
| 6,093,200 A | 7/2000 | Liu et al. |
| 6,093,201 A * | 7/2000 | Cooper ............... A61B 17/80 606/232 |
| 6,096,060 A | 8/2000 | Fitts et al. |
| 6,099,527 A | 8/2000 | Hochschuler et al. |
| 6,099,530 A | 8/2000 | Simonian et al. |
| 6,099,568 A | 8/2000 | Simonian et al. |
| 6,102,934 A | 8/2000 | Li |
| 6,106,545 A | 8/2000 | Egan |
| 6,110,128 A | 8/2000 | Andelin et al. |
| 6,113,604 A | 9/2000 | Whittaker et al. |
| 6,117,160 A | 9/2000 | Bonutti |
| 6,117,162 A | 9/2000 | Schmieding et al. |
| 6,123,710 A | 9/2000 | Pinczewski et al. |
| 6,132,433 A | 10/2000 | Whelan |
| 6,132,437 A | 10/2000 | Omurtag et al. |
| 6,139,565 A | 10/2000 | Stone et al. |
| RE36,974 E | 11/2000 | Bonutti |
| 6,143,017 A | 11/2000 | Thal |
| 6,146,406 A | 11/2000 | Shluzas et al. |
| 6,146,408 A | 11/2000 | Bartlett |
| 6,149,653 A | 11/2000 | Deslauriers |
| 6,149,669 A | 11/2000 | Li |
| 6,152,928 A | 11/2000 | Wenstrom, Jr. |
| 6,152,934 A | 11/2000 | Harper et al. |
| 6,152,936 A | 11/2000 | Christy et al. |
| 6,152,949 A | 11/2000 | Bonutti |
| 6,156,039 A | 12/2000 | Thal |
| 6,156,056 A * | 12/2000 | Kearns ............... A61B 17/0469 606/232 |
| 6,159,234 A | 12/2000 | Bonutti et al. |
| 6,165,203 A | 12/2000 | Krebs |
| 6,168,598 B1 | 1/2001 | Martello |
| 6,168,628 B1 | 1/2001 | Huebner |

(56) References Cited

U.S. PATENT DOCUMENTS

| | | |
|---|---|---|
| 6,171,310 B1 | 1/2001 | Giordano et al. |
| 6,179,840 B1 | 1/2001 | Bowman |
| 6,183,461 B1 | 2/2001 | Matsuura et al. |
| 6,187,025 B1 | 2/2001 | Machek |
| 6,190,401 B1 | 2/2001 | Green et al. |
| 6,190,411 B1 | 2/2001 | Lo et al. |
| 6,193,754 B1 | 2/2001 | Seedhom |
| 6,200,318 B1 | 3/2001 | Har-Shai et al. |
| 6,200,329 B1 | 3/2001 | Fung et al. |
| 6,200,330 B1 | 3/2001 | Benderev et al. |
| 6,203,556 B1 | 3/2001 | Evans et al. |
| 6,203,565 B1 | 3/2001 | Bonutti et al. |
| 6,203,572 B1 | 3/2001 | Johnson et al. |
| 6,206,883 B1 | 3/2001 | Tunc |
| 6,210,376 B1 | 4/2001 | Grayson |
| 6,214,007 B1 | 4/2001 | Anderson |
| 6,214,012 B1 | 4/2001 | Karpman et al. |
| 6,217,580 B1 | 4/2001 | Levin |
| 6,221,107 B1 | 4/2001 | Steiner et al. |
| 6,228,096 B1 | 5/2001 | Marchand |
| 6,231,592 B1 | 5/2001 | Bonutti et al. |
| 6,235,057 B1 | 5/2001 | Roger et al. |
| 6,238,395 B1 | 5/2001 | Bonutti |
| 6,241,734 B1 | 6/2001 | Scribner et al. |
| 6,241,747 B1 | 6/2001 | Ruff |
| 6,241,771 B1 | 6/2001 | Gresser et al. |
| 6,245,081 B1 | 6/2001 | Bowman et al. |
| 6,254,604 B1 | 7/2001 | Howell |
| 6,258,091 B1 | 7/2001 | Sevrain et al. |
| 6,267,766 B1 | 7/2001 | Burkhart |
| 6,269,716 B1 | 8/2001 | Amis |
| 6,270,518 B1 | 8/2001 | Pedlick et al. |
| 6,273,890 B1 | 8/2001 | Frazier |
| 6,280,474 B1 | 8/2001 | Cassidy et al. |
| 6,283,973 B1 | 9/2001 | Hubbard et al. |
| 6,283,996 B1 | 9/2001 | Chervitz et al. |
| 6,287,307 B1 | 9/2001 | Abboudi |
| 6,287,325 B1 | 9/2001 | Bonutti |
| 6,293,961 B2 | 9/2001 | Schwartz et al. |
| 6,296,483 B1 * | 10/2001 | Champleboux ........ A61C 1/084 433/75 |
| 6,296,659 B1 | 10/2001 | Foerster |
| 6,299,615 B1 | 10/2001 | Huebner |
| 6,302,888 B1 | 10/2001 | Mellinger et al. |
| 6,302,899 B1 | 10/2001 | Johnson et al. |
| 6,303,158 B1 | 10/2001 | Odgaard et al. |
| 6,306,156 B1 | 10/2001 | Clark |
| 6,306,158 B1 | 10/2001 | Bartlett |
| 6,306,159 B1 | 10/2001 | Schwartz et al. |
| 6,309,405 B1 | 10/2001 | Bonutti |
| 6,312,448 B1 | 11/2001 | Bonutti |
| 6,315,788 B1 | 11/2001 | Roby |
| 6,319,271 B1 | 11/2001 | Schwartz et al. |
| 6,327,491 B1 * | 12/2001 | Franklin .................. 600/429 |
| 6,328,758 B1 | 12/2001 | Tornier et al. |
| 6,342,060 B1 | 1/2002 | Adams |
| 6,343,531 B2 | 2/2002 | Amis |
| 6,355,066 B1 | 3/2002 | Kim |
| 6,358,270 B1 | 3/2002 | Lemer |
| 6,364,897 B1 | 4/2002 | Bonutti |
| 6,368,322 B1 | 4/2002 | Luks et al. |
| 6,368,326 B1 | 4/2002 | Dakin et al. |
| 6,368,343 B1 | 4/2002 | Bonutti et al. |
| 6,371,124 B1 | 4/2002 | Whelan |
| 6,379,361 B1 | 4/2002 | Beck, Jr. et al. |
| 6,383,190 B1 | 5/2002 | Preissman |
| 6,383,199 B2 | 5/2002 | Carter et al. |
| 6,387,113 B1 | 5/2002 | Hawkins et al. |
| 6,387,129 B2 | 5/2002 | Rieser et al. |
| 6,391,030 B1 | 5/2002 | Wagner et al. |
| 6,398,785 B2 | 6/2002 | Carchidi et al. |
| 6,406,479 B1 | 6/2002 | Justin et al. |
| 6,409,743 B1 | 6/2002 | Fenton, Jr. |
| 6,413,260 B1 | 7/2002 | Berrevoets et al. |
| 6,423,073 B2 | 7/2002 | Bowman |
| 6,423,088 B1 | 7/2002 | Fenton, Jr. |
| 6,428,562 B2 | 8/2002 | Bonutti |
| 6,432,123 B2 | 8/2002 | Schwartz et al. |
| 6,436,123 B1 | 8/2002 | Magovern |
| 6,436,124 B1 | 8/2002 | Anderson et al. |
| 6,440,134 B1 | 8/2002 | Zaccherotti et al. |
| 6,440,136 B1 | 8/2002 | Gambale et al. |
| 6,447,516 B1 | 9/2002 | Bonutti |
| 6,451,030 B2 | 9/2002 | Li et al. |
| 6,454,768 B1 | 9/2002 | Jackson |
| 6,458,134 B1 | 10/2002 | Songer et al. |
| 6,461,373 B2 | 10/2002 | Wyman et al. |
| 6,464,690 B1 | 10/2002 | Castaneda et al. |
| 6,464,713 B2 | 10/2002 | Bonutti |
| 6,468,293 B2 | 10/2002 | Bonutti et al. |
| 6,471,707 B1 | 10/2002 | Miller et al. |
| 6,475,230 B1 | 11/2002 | Bonutti et al. |
| 6,478,753 B2 | 11/2002 | Reay-Young |
| 6,482,210 B1 | 11/2002 | Skiba et al. |
| 6,485,504 B1 | 11/2002 | Johnson et al. |
| 6,491,714 B1 | 12/2002 | Bennett |
| 6,497,901 B1 | 12/2002 | Royer |
| 6,500,184 B1 | 12/2002 | Chan et al. |
| 6,500,195 B2 | 12/2002 | Bonutti |
| RE37,963 E | 1/2003 | Thal |
| 6,503,267 B2 | 1/2003 | Bonutti et al. |
| 6,506,190 B1 | 1/2003 | Walshe |
| 6,508,820 B2 | 1/2003 | Bales |
| 6,508,821 B1 | 1/2003 | Schwartz et al. |
| 6,508,830 B2 | 1/2003 | Steiner |
| 6,511,498 B1 | 1/2003 | Fumex |
| 6,511,499 B2 | 1/2003 | Schmieding et al. |
| 6,517,542 B1 | 2/2003 | Papay et al. |
| 6,517,552 B1 | 2/2003 | Nord et al. |
| 6,517,564 B1 | 2/2003 | Grafton et al. |
| 6,517,578 B2 | 2/2003 | Hein |
| 6,517,579 B1 | 2/2003 | Paulos et al. |
| 6,520,964 B2 | 2/2003 | Tallarida et al. |
| 6,520,980 B1 | 2/2003 | Foerster |
| 6,524,317 B1 | 2/2003 | Ritchart et al. |
| 6,527,777 B2 | 3/2003 | Justin |
| 6,527,794 B1 | 3/2003 | McDevitt et al. |
| 6,527,795 B1 | 3/2003 | Lizardi |
| 6,533,795 B1 | 3/2003 | Tran et al. |
| 6,533,802 B2 | 3/2003 | Bojarski et al. |
| 6,537,319 B2 | 3/2003 | Whelan |
| 6,540,750 B2 | 4/2003 | Burkhart |
| 6,540,769 B1 | 4/2003 | Miller, III |
| 6,540,770 B1 | 4/2003 | Tornier et al. |
| 6,540,783 B1 | 4/2003 | Whittaker et al. |
| 6,543,094 B2 | 4/2003 | D'Addario |
| 6,544,281 B2 | 4/2003 | ElAttrache et al. |
| 6,547,564 B1 | 4/2003 | Hansson et al. |
| 6,547,778 B1 | 4/2003 | Sklar et al. |
| 6,547,800 B2 | 4/2003 | Foerster et al. |
| 6,551,330 B1 | 4/2003 | Bain et al. |
| 6,551,343 B1 | 4/2003 | Tormala et al. |
| 6,553,802 B1 | 4/2003 | Jacob et al. |
| 6,554,830 B1 | 4/2003 | Chappius |
| 6,554,852 B1 | 4/2003 | Oberlander |
| 6,554,862 B2 | 4/2003 | Hays et al. |
| 6,558,389 B2 | 5/2003 | Clark et al. |
| 6,562,071 B2 | 5/2003 | Jarvinen et al. |
| 6,565,572 B2 | 5/2003 | Chappius |
| 6,565,573 B1 | 5/2003 | Ferrante et al. |
| 6,569,186 B1 | 5/2003 | Winters et al. |
| 6,569,187 B1 | 5/2003 | Bonutti et al. |
| 6,572,635 B1 | 6/2003 | Bonutti |
| 6,575,925 B1 | 6/2003 | Noble |
| 6,579,295 B1 | 6/2003 | Supinski |
| 6,582,453 B1 | 6/2003 | Tran et al. |
| 6,585,730 B1 | 7/2003 | Foerster |
| 6,585,740 B2 | 7/2003 | Schlapfer et al. |
| 6,585,750 B2 | 7/2003 | Bonutti et al. |
| 6,589,245 B1 | 7/2003 | Weiler et al. |
| 6,589,246 B1 | 7/2003 | Hack et al. |
| 6,592,609 B1 | 7/2003 | Bonutti |
| 6,595,911 B2 | 7/2003 | LoVuolo |
| 6,599,289 B1 | 7/2003 | Bojarski et al. |

(56) References Cited

U.S. PATENT DOCUMENTS

| | | | |
|---|---|---|---|
| 6,599,319 B2 | 7/2003 | Knudsen et al. |
| 6,605,096 B1 | 8/2003 | Ritchart |
| 6,607,548 B2 | 8/2003 | Pohjonen et al. |
| 6,610,079 B1 | 8/2003 | Li et al. |
| 6,613,018 B2 | 9/2003 | Bagga et al. |
| 6,616,694 B1 | 9/2003 | Hart |
| 6,620,166 B1 | 9/2003 | Wenstrom, Jr. et al. |
| 6,620,185 B1 | 9/2003 | Harvie et al. |
| 6,620,195 B2 | 9/2003 | Goble et al. |
| 6,620,329 B2 | 9/2003 | Rosen et al. |
| 6,620,349 B1 | 9/2003 | Lopez |
| 6,623,492 B1 | 9/2003 | Berube et al. |
| 6,623,524 B2 | 9/2003 | Schmieding |
| 6,626,910 B1 | 9/2003 | Hugues |
| 6,626,919 B1 | 9/2003 | Swanstrom |
| 6,629,977 B1 | 10/2003 | Wolf |
| 6,632,245 B2 | 10/2003 | Kim |
| 6,635,073 B2 | 10/2003 | Bonutti |
| 6,638,279 B2 | 10/2003 | Bonutti |
| 6,638,312 B2 | 10/2003 | Plouhar et al. |
| 6,641,596 B1 | 11/2003 | Lizardi |
| 6,641,597 B2 | 11/2003 | Burkhart et al. |
| 6,645,211 B2 | 11/2003 | Magana |
| 6,645,227 B2 | 11/2003 | Fallin et al. |
| 6,648,921 B2 | 11/2003 | Anderson et al. |
| 6,652,450 B2 | 11/2003 | Neisz et al. |
| 6,652,560 B1 | 11/2003 | Gerke et al. |
| 6,652,562 B2 | 11/2003 | Collier et al. |
| 6,652,563 B2 | 11/2003 | Dreyfuss |
| 6,656,182 B1 | 12/2003 | Hayhurst |
| 6,656,183 B2 | 12/2003 | Colleran et al. |
| 6,658,182 B1 | 12/2003 | Gonthier et al. |
| 6,660,008 B1 | 12/2003 | Foerster et al. |
| 6,660,022 B1 | 12/2003 | Li et al. |
| 6,663,634 B2 | 12/2003 | Ahrens et al. |
| 6,663,656 B2 | 12/2003 | Schmieding et al. |
| 6,666,868 B2 | 12/2003 | Fallin |
| 6,666,877 B2 | 12/2003 | Morgan et al. |
| 6,679,889 B1 | 1/2004 | West, Jr. et al. |
| 6,682,533 B1 | 1/2004 | Dinsdale et al. |
| 6,682,549 B2 | 1/2004 | Bartlett |
| 6,685,728 B2 | 2/2004 | Sinnott et al. |
| 6,689,137 B2 | 2/2004 | Reed |
| 6,689,153 B1 | 2/2004 | Skiba |
| 6,689,154 B2 | 2/2004 | Bartlett |
| 6,692,499 B2 | 2/2004 | Tormala et al. |
| 6,692,516 B2 | 2/2004 | West, Jr. et al. |
| 6,695,852 B2 | 2/2004 | Gleason |
| 6,712,849 B2 | 3/2004 | Re et al. |
| 6,716,224 B2 | 4/2004 | Singhatat |
| 6,716,957 B2 | 4/2004 | Tunc |
| 6,730,092 B2 | 5/2004 | Songer |
| 6,730,124 B2 | 5/2004 | Steiner |
| 6,736,799 B1 | 5/2004 | Erbe et al. |
| 6,737,053 B1 | 5/2004 | Goh et al. |
| 6,746,483 B1 | 6/2004 | Bojarski et al. |
| 6,752,810 B1 | 6/2004 | Gao et al. |
| 6,752,831 B2 | 6/2004 | Sybert et al. |
| 6,755,836 B1 | 6/2004 | Lewis |
| 6,761,722 B2 | 7/2004 | Cole et al. |
| 6,761,739 B2 | 7/2004 | Shepard |
| 6,767,037 B2 | 7/2004 | Wenstrom, Jr. |
| 6,770,076 B2 | 8/2004 | Foerster |
| 6,770,084 B1 | 8/2004 | Bain et al. |
| 6,773,450 B2 | 8/2004 | Leung et al. |
| 6,779,701 B2 | 8/2004 | Bailly et al. |
| 6,780,190 B2 | 8/2004 | Maroney |
| 6,780,198 B1 | 8/2004 | Gregoire et al. |
| 6,793,595 B1 | 9/2004 | Monnet |
| 6,802,862 B1 | 10/2004 | Roger et al. |
| 6,808,502 B2 | 10/2004 | Nguyen et al. |
| 6,808,526 B1 | 10/2004 | Magerl et al. |
| 6,814,741 B2 | 11/2004 | Bowman et al. |
| 6,830,572 B2 | 12/2004 | McDevitt et al. |
| 6,833,005 B1 | 12/2004 | Mantas et al. |
| 6,840,953 B2 | 1/2005 | Martinek |
| 6,860,885 B2 | 3/2005 | Bonutti |
| 6,860,895 B1 | 3/2005 | Akerfeldt et al. |
| 6,863,671 B1 | 3/2005 | Strobel et al. |
| 6,872,040 B2 | 3/2005 | Deeg et al. |
| 6,872,210 B2 | 3/2005 | Hearn |
| 6,875,216 B2 | 4/2005 | Wolf |
| 6,884,249 B2 | 4/2005 | May et al. |
| 6,887,259 B2 | 5/2005 | Lizardi |
| 6,887,271 B2 | 5/2005 | Justin et al. |
| 6,890,354 B2 | 5/2005 | Steiner et al. |
| 6,893,448 B2 | 5/2005 | O'Quinn et al. |
| 6,896,686 B2 | 5/2005 | Weber |
| 6,899,722 B2 | 5/2005 | Bonutti |
| 6,902,573 B2 | 6/2005 | Strobel et al. |
| 6,905,513 B1 | 6/2005 | Metzger |
| 6,908,466 B1 | 6/2005 | Bonutti et al. |
| 6,913,463 B2 * | 7/2005 | Blacklock | A61B 17/176 |
| | | | 408/115 R |
| 6,916,292 B2 | 7/2005 | Morawski et al. |
| 6,916,321 B2 | 7/2005 | TenHuisen et al. |
| 6,921,402 B2 | 7/2005 | Contiliano et al. |
| 6,923,823 B1 | 8/2005 | Bartlett et al. |
| 6,923,824 B2 | 8/2005 | Morgan et al. |
| 6,939,379 B2 | 9/2005 | Sklar |
| 6,949,102 B2 | 9/2005 | Andrews |
| 6,951,565 B2 | 10/2005 | Keane et al. |
| 6,966,887 B1 | 11/2005 | Chin |
| 6,966,916 B2 | 11/2005 | Kumar |
| 6,969,391 B1 | 11/2005 | Gazzani |
| 6,969,398 B2 | 11/2005 | Stevens et al. |
| 6,972,027 B2 | 12/2005 | Fallin et al. |
| 6,980,903 B2 | 12/2005 | Daniels et al. |
| 6,984,237 B2 | 1/2006 | Hatch et al. |
| 6,986,781 B2 | 1/2006 | Smith |
| 6,989,034 B2 | 1/2006 | Hammer et al. |
| 6,994,719 B2 | 2/2006 | Grafton |
| 6,994,725 B1 | 2/2006 | Goble |
| 7,001,429 B2 | 2/2006 | Ferguson |
| 7,004,959 B2 | 2/2006 | Bonutti |
| 7,008,451 B2 | 3/2006 | Justin et al. |
| 7,048,754 B2 | 5/2006 | Martin et al. |
| 7,052,499 B2 | 5/2006 | Steger et al. |
| 7,066,942 B2 | 6/2006 | Treace |
| 7,066,944 B2 | 6/2006 | Laufer et al. |
| 7,081,126 B2 | 7/2006 | McDevitt et al. |
| 7,087,064 B1 | 8/2006 | Hyde |
| 7,097,654 B1 | 8/2006 | Freedland |
| 7,105,010 B2 | 9/2006 | Hart et al. |
| 7,112,221 B2 | 9/2006 | Harris et al. |
| 7,118,578 B2 | 10/2006 | West, Jr. et al. |
| 7,118,583 B2 | 10/2006 | O'Quinn et al. |
| 7,125,421 B2 | 10/2006 | Tremulis et al. |
| 7,131,467 B2 | 11/2006 | Gao et al. |
| 7,137,996 B2 | 11/2006 | Steiner et al. |
| 7,141,066 B2 | 11/2006 | Steiner et al. |
| 7,144,414 B2 | 12/2006 | Harvie et al. |
| 7,153,127 B2 | 12/2006 | Struble et al. |
| 7,153,307 B2 | 12/2006 | Scribner et al. |
| 7,153,312 B1 | 12/2006 | Torrie et al. |
| 7,153,327 B1 | 12/2006 | Metzger |
| 7,160,285 B2 | 1/2007 | Sklar et al. |
| 7,160,333 B2 | 1/2007 | Plouhar et al. |
| 7,172,626 B1 | 2/2007 | Andrews |
| 7,201,722 B2 | 4/2007 | Krueger |
| 7,207,993 B1 | 4/2007 | Baldwin et al. |
| 7,255,675 B2 | 8/2007 | Gertner et al. |
| 7,255,700 B2 | 8/2007 | Kaiser et al. |
| 7,255,715 B2 | 8/2007 | Metzger |
| 7,261,716 B2 | 8/2007 | Strobel et al. |
| 7,264,634 B2 | 9/2007 | Schmieding |
| 7,279,008 B2 | 10/2007 | Brown et al. |
| 7,285,124 B2 | 10/2007 | Foerster |
| 7,303,577 B1 | 12/2007 | Dean |
| 7,306,417 B2 | 12/2007 | Dorstewitz |
| 7,309,355 B2 | 12/2007 | Donnelly et al. |
| 7,326,222 B2 | 2/2008 | Dreyfuss et al. |
| 7,329,272 B2 | 2/2008 | Burkhart et al. |
| 7,361,179 B2 | 4/2008 | Rousseau et al. |

(56) References Cited

U.S. PATENT DOCUMENTS

| | | | |
|---|---|---|---|
| 7,377,845 B2 | 5/2008 | Stewart et al. |
| 7,390,329 B2 | 6/2008 | Westra et al. |
| 7,390,332 B2 | 6/2008 | Selvitelli et al. |
| 7,399,018 B1 | 7/2008 | Khachaturian |
| 7,442,210 B2 | 10/2008 | Segal et al. |
| 7,465,308 B2 | 12/2008 | Sikora et al. |
| 7,468,074 B2 | 12/2008 | Caborn et al. |
| 7,494,506 B2 | 2/2009 | Brulez et al. |
| D587,807 S | 3/2009 | Wolf et al. |
| 7,500,983 B1 | 3/2009 | Kaiser et al. |
| 7,513,910 B2 | 4/2009 | Buskirk et al. |
| 7,572,298 B2 | 8/2009 | Roller et al. |
| 7,578,825 B2 | 8/2009 | Huebner |
| 7,585,311 B2 | 9/2009 | Green et al. |
| 7,591,823 B2 | 9/2009 | Tipirneni |
| 7,597,705 B2 | 10/2009 | Forsberg et al. |
| 7,601,165 B2 | 10/2009 | Stone |
| 7,604,636 B1 | 10/2009 | Walters et al. |
| 7,608,092 B1 | 10/2009 | Schaffhausen |
| 7,608,098 B1 | 10/2009 | Stone et al. |
| 7,615,076 B2 | 11/2009 | Cauthen, III et al. |
| 7,621,937 B2 | 11/2009 | Pipenhagen et al. |
| 7,632,287 B2 | 12/2009 | Baker et al. |
| 7,651,509 B2 | 1/2010 | Bojarski et al. |
| 7,658,750 B2 | 2/2010 | Li |
| 7,658,751 B2 | 2/2010 | Stone et al. |
| 7,670,279 B2 | 3/2010 | Gertner |
| 7,678,123 B2 | 3/2010 | Chanduszko |
| 7,695,493 B2 | 4/2010 | Saadat et al. |
| 7,695,503 B1 | 4/2010 | Kaiser et al. |
| 7,717,929 B2 | 5/2010 | Fallman |
| 7,731,732 B2 | 6/2010 | Ken |
| 7,736,364 B2 | 6/2010 | Stone |
| 7,736,379 B2 | 6/2010 | Ewers et al. |
| 7,749,250 B2 | 7/2010 | Stone et al. |
| 7,758,594 B2 | 7/2010 | Lamson et al. |
| 7,758,611 B2 | 7/2010 | Kato |
| 7,776,041 B1 | 8/2010 | Walters |
| 7,803,173 B2 | 9/2010 | Burkhart et al. |
| 7,819,895 B2 | 10/2010 | Ginn et al. |
| 7,828,820 B2 | 11/2010 | Stone et al. |
| 7,828,850 B2 | 11/2010 | Cauthen, III et al. |
| 7,856,698 B2 | 12/2010 | Hays |
| 7,857,830 B2 | 12/2010 | Stone et al. |
| 7,867,264 B2 | 1/2011 | McDevitt et al. |
| 7,875,058 B2 | 1/2011 | Holmes, Jr. |
| 7,878,058 B2 | 2/2011 | Blendinger et al. |
| 7,887,586 B2 | 2/2011 | Linares |
| 7,905,903 B2 | 3/2011 | Stone et al. |
| 7,905,904 B2 | 3/2011 | Stone et al. |
| 7,909,851 B2 | 3/2011 | Stone et al. |
| 7,938,847 B2 | 5/2011 | Fanton et al. |
| 7,959,650 B2 | 6/2011 | Kaiser et al. |
| 7,963,968 B2 * | 6/2011 | Dees, Jr. ............ A61B 17/1675 606/87 |
| 7,981,140 B2 | 7/2011 | Burkhart |
| 7,998,203 B2 | 8/2011 | Blum |
| 8,062,334 B2 | 11/2011 | Green et al. |
| 8,075,574 B2 | 12/2011 | May et al. |
| 8,088,130 B2 | 1/2012 | Kaiser et al. |
| 8,114,127 B2 | 2/2012 | West, Jr. |
| 8,114,128 B2 | 2/2012 | Cauldwell et al. |
| 8,118,835 B2 | 2/2012 | Weisel et al. |
| 8,118,836 B2 | 2/2012 | Denham et al. |
| 8,128,658 B2 | 3/2012 | Kaiser et al. |
| 8,137,354 B2 | 3/2012 | Stone |
| 8,137,382 B2 | 3/2012 | Denham et al. |
| 8,162,997 B2 | 4/2012 | Struhl |
| 8,167,906 B2 | 5/2012 | Cauldwell et al. |
| 8,202,318 B2 | 6/2012 | Willobee |
| 8,221,454 B2 | 7/2012 | Schaffhausen |
| 8,231,654 B2 | 7/2012 | Kaiser et al. |
| 8,251,998 B2 | 8/2012 | Hoeppner et al. |
| 8,252,022 B2 | 8/2012 | Holman et al. |
| 8,273,106 B2 | 9/2012 | Stone et al. |
| 8,292,921 B2 | 10/2012 | Stone et al. |
| 8,298,262 B2 | 10/2012 | Stone et al. |
| 8,298,284 B2 | 10/2012 | Cassani |
| 8,303,604 B2 | 11/2012 | Stone et al. |
| 8,317,825 B2 | 11/2012 | Stone |
| 8,337,525 B2 | 12/2012 | Stone et al. |
| 8,343,155 B2 | 1/2013 | Fisher et al. |
| 8,343,227 B2 | 1/2013 | Metzger et al. |
| 8,361,113 B2 | 1/2013 | Stone et al. |
| 8,409,253 B2 | 4/2013 | Stone et al. |
| 8,486,114 B2 | 7/2013 | Gillard et al. |
| 8,500,818 B2 | 8/2013 | Metzger et al. |
| 8,506,597 B2 | 8/2013 | Kaiser et al. |
| 8,551,140 B2 | 10/2013 | Denham et al. |
| 8,562,645 B2 | 10/2013 | Stone et al. |
| 8,562,647 B2 | 10/2013 | Kaiser et al. |
| 8,597,327 B2 | 12/2013 | Stone et al. |
| 8,608,777 B2 | 12/2013 | Kaiser et al. |
| 8,632,566 B2 | 1/2014 | Olson |
| 8,632,569 B2 | 1/2014 | Stone et al. |
| 8,652,171 B2 | 2/2014 | Stone et al. |
| 8,652,172 B2 | 2/2014 | Denham et al. |
| 8,672,968 B2 | 3/2014 | Stone et al. |
| 8,672,969 B2 | 3/2014 | Stone et al. |
| 8,721,650 B2 | 5/2014 | Fanton et al. |
| 8,721,684 B2 | 5/2014 | Denham et al. |
| 8,753,379 B1 * | 6/2014 | Frei ............ A61B 17/1735 606/285 |
| 8,771,316 B2 | 7/2014 | Denham et al. |
| 8,771,352 B2 | 7/2014 | Conner et al. |
| 8,777,956 B2 | 7/2014 | Hoeppner et al. |
| 8,801,783 B2 | 8/2014 | Stone et al. |
| 8,814,902 B2 * | 8/2014 | Bonutti ............ A61B 17/0401 606/232 |
| 8,840,645 B2 | 9/2014 | Denham et al. |
| 8,900,314 B2 | 12/2014 | Metzger et al. |
| 8,932,331 B2 | 1/2015 | Kaiser et al. |
| 8,936,621 B2 | 1/2015 | Denham et al. |
| 8,968,364 B2 | 3/2015 | Berelsman et al. |
| 8,998,949 B2 | 4/2015 | Stone et al. |
| 9,005,287 B2 | 4/2015 | Stone |
| 9,017,381 B2 | 4/2015 | Kaiser et al. |
| 2001/0010005 A1 | 7/2001 | Kammerer et al. |
| 2001/0014825 A1 | 8/2001 | Burke et al. |
| 2001/0019649 A1 | 9/2001 | Field et al. |
| 2001/0029387 A1 | 10/2001 | Wolf et al. |
| 2001/0037131 A1 | 11/2001 | Schmieding et al. |
| 2001/0037153 A1 | 11/2001 | Rockwood et al. |
| 2001/0041916 A1 | 11/2001 | Bonutti |
| 2001/0041937 A1 | 11/2001 | Rieser et al. |
| 2001/0041938 A1 | 11/2001 | Hein |
| 2001/0044639 A1 | 11/2001 | Levinson |
| 2001/0047206 A1 | 11/2001 | Sklar et al. |
| 2001/0051816 A1 | 12/2001 | Enzerink et al. |
| 2001/0053934 A1 | 12/2001 | Schmieding |
| 2002/0001964 A1 | 1/2002 | Choi |
| 2002/0004669 A1 | 1/2002 | Bartlett |
| 2002/0007182 A1 | 1/2002 | Kim |
| 2002/0010513 A1 | 1/2002 | Schmieding |
| 2002/0013607 A1 | 1/2002 | Lemer |
| 2002/0013608 A1 | 1/2002 | ElAttrache et al. |
| 2002/0019649 A1 | 2/2002 | Sikora et al. |
| 2002/0029066 A1 | 3/2002 | Foerster |
| 2002/0032465 A1 | 3/2002 | Lemer |
| 2002/0055780 A1 | 5/2002 | Sklar |
| 2002/0058966 A1 | 5/2002 | Tormala et al. |
| 2002/0068254 A1 | 6/2002 | Campbell |
| 2002/0077659 A1 | 6/2002 | Johnson et al. |
| 2002/0099411 A1 | 7/2002 | Bartlett |
| 2002/0111653 A1 | 8/2002 | Foerster |
| 2002/0120270 A1 | 8/2002 | Trieu et al. |
| 2002/0120292 A1 | 8/2002 | Morgan |
| 2002/0123752 A1 | 9/2002 | Schultheiss et al. |
| 2002/0128654 A1 | 9/2002 | Steger et al. |
| 2002/0128684 A1 | 9/2002 | Foerster |
| 2002/0129820 A1 | 9/2002 | Ryan et al. |
| 2002/0143336 A1 | 10/2002 | Hearn |
| 2002/0147463 A1 | 10/2002 | Martinek |
| 2002/0156475 A1 | 10/2002 | Lerch et al. |

(56) References Cited

U.S. PATENT DOCUMENTS

| | | |
|---|---|---|
| 2002/0161401 A1 | 10/2002 | Steiner |
| 2002/0161439 A1 | 10/2002 | Strobel et al. |
| 2002/0165548 A1 | 11/2002 | Jutley |
| 2002/0165611 A1 | 11/2002 | Enzerink et al. |
| 2002/0169452 A1 | 11/2002 | Tormala et al. |
| 2002/0169477 A1 | 11/2002 | Demopulos et al. |
| 2002/0169478 A1 | 11/2002 | Schwartz et al. |
| 2002/0173788 A1 | 11/2002 | Bojarski et al. |
| 2002/0177853 A1 | 11/2002 | Chervitz et al. |
| 2002/0188298 A1 | 12/2002 | Chan |
| 2002/0193830 A1 | 12/2002 | Bonutti |
| 2003/0004545 A1 | 1/2003 | Burkhart et al. |
| 2003/0009235 A1 | 1/2003 | Manrique et al. |
| 2003/0023268 A1 | 1/2003 | Lizardi |
| 2003/0032961 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0065391 A1 | 4/2003 | Re et al. |
| 2003/0065402 A1 | 4/2003 | Anderson et al. |
| 2003/0078585 A1 | 4/2003 | Johnson et al. |
| 2003/0078603 A1 | 4/2003 | Schaller et al. |
| 2003/0078617 A1 | 4/2003 | Schwartz et al. |
| 2003/0083662 A1 | 5/2003 | Middleton |
| 2003/0083694 A1 | 5/2003 | Miller |
| 2003/0088251 A1 | 5/2003 | Braun et al. |
| 2003/0088272 A1 | 5/2003 | Smith |
| 2003/0105477 A1 | 6/2003 | Schwartz et al. |
| 2003/0105489 A1 | 6/2003 | Eichhorn et al. |
| 2003/0120309 A1 | 6/2003 | Colleran et al. |
| 2003/0130670 A1 | 7/2003 | Anderson et al. |
| 2003/0130694 A1 | 7/2003 | Bojarski et al. |
| 2003/0130695 A1 | 7/2003 | McDevitt et al. |
| 2003/0135214 A1 | 7/2003 | Fetto et al. |
| 2003/0135239 A1 | 7/2003 | Gabriel et al. |
| 2003/0135963 A1 | 7/2003 | Holbrook et al. |
| 2003/0139775 A1 | 7/2003 | Grafton |
| 2003/0149448 A1 | 8/2003 | Foerster et al. |
| 2003/0152522 A1 | 8/2003 | Miller et al. |
| 2003/0153947 A1 | 8/2003 | Koseki |
| 2003/0167072 A1 | 9/2003 | Oberlander |
| 2003/0167090 A1 | 9/2003 | Chervitz et al. |
| 2003/0171811 A1 | 9/2003 | Steiner et al. |
| 2003/0176865 A1 | 9/2003 | Supinski |
| 2003/0176919 A1 | 9/2003 | Schmieding |
| 2003/0176920 A1 | 9/2003 | Sklar et al. |
| 2003/0181925 A1 | 9/2003 | Bain et al. |
| 2003/0195528 A1 | 10/2003 | Ritchart |
| 2003/0195564 A1 | 10/2003 | Tran et al. |
| 2003/0208210 A1 | 11/2003 | Dreyfuss et al. |
| 2003/0212456 A1 | 11/2003 | Lipchitz et al. |
| 2003/0216809 A1 | 11/2003 | Ferguson |
| 2003/0220660 A1 | 11/2003 | Kortenbach et al. |
| 2003/0225459 A1 | 12/2003 | Hammer et al. |
| 2003/0229396 A1 | 12/2003 | Andrews |
| 2004/0002734 A1 | 1/2004 | Fallin et al. |
| 2004/0006345 A1 | 1/2004 | Vlahos et al. |
| 2004/0006346 A1 | 1/2004 | Holmen et al. |
| 2004/0015171 A1 | 1/2004 | Bojarski et al. |
| 2004/0015172 A1 | 1/2004 | Biedermann et al. |
| 2004/0024456 A1 | 2/2004 | Brown et al. |
| 2004/0024457 A1 | 2/2004 | Boyce et al. |
| 2004/0039389 A1 | 2/2004 | West et al. |
| 2004/0044391 A1 | 3/2004 | Porter |
| 2004/0059357 A1 | 3/2004 | Koseki |
| 2004/0087981 A1 | 5/2004 | Berube et al. |
| 2004/0092936 A1 | 5/2004 | Miller et al. |
| 2004/0093031 A1 | 5/2004 | Burkhart et al. |
| 2004/0093032 A1 | 5/2004 | Sinnott et al. |
| 2004/0098051 A1 | 5/2004 | Fallin et al. |
| 2004/0098053 A1 | 5/2004 | Tran |
| 2004/0111117 A1 | 6/2004 | Colleran et al. |
| 2004/0122431 A1 | 6/2004 | Biedermann et al. |
| 2004/0133206 A1 | 7/2004 | Stevens et al. |
| 2004/0133211 A1 | 7/2004 | Raskin et al. |
| 2004/0138664 A1 | 7/2004 | Bowman |
| 2004/0138683 A1 | 7/2004 | Shelton et al. |
| 2004/0138704 A1 | 7/2004 | Gambale et al. |
| 2004/0138706 A1 | 7/2004 | Abrams et al. |
| 2004/0138747 A1 | 7/2004 | Kaladelfos |
| 2004/0143344 A1 | 7/2004 | Malaviya et al. |
| 2004/0147932 A1 | 7/2004 | Burkinshaw et al. |
| 2004/0147958 A1 | 7/2004 | Lam et al. |
| 2004/0153103 A1 | 8/2004 | Schwartz et al. |
| 2004/0153153 A1 | 8/2004 | Elson et al. |
| 2004/0162579 A1 | 8/2004 | Foerster |
| 2004/0166169 A1 | 8/2004 | Malaviya et al. |
| 2004/0181234 A1 | 9/2004 | McDevitt et al. |
| 2004/0182968 A1 | 9/2004 | Gentry |
| 2004/0187314 A1 | 9/2004 | Johnson |
| 2004/0193185 A1 | 9/2004 | McBrayer |
| 2004/0199169 A1 | 10/2004 | Koons et al. |
| 2004/0204722 A1 | 10/2004 | Sikora et al. |
| 2004/0220574 A1 | 11/2004 | Pelo et al. |
| 2004/0225183 A1 | 11/2004 | Michlitsch et al. |
| 2004/0225292 A1 | 11/2004 | Sasso et al. |
| 2004/0225305 A1 | 11/2004 | Ewers et al. |
| 2004/0236353 A1 | 11/2004 | Bain et al. |
| 2004/0236373 A1 | 11/2004 | Anspach |
| 2004/0243139 A1 | 12/2004 | Lewis et al. |
| 2004/0243178 A1 | 12/2004 | Haut et al. |
| 2004/0243180 A1 | 12/2004 | Donnelly et al. |
| 2004/0243235 A1 | 12/2004 | Goh et al. |
| 2004/0249394 A1 | 12/2004 | Morris et al. |
| 2004/0260296 A1 | 12/2004 | Kaiser et al. |
| 2004/0260298 A1 | 12/2004 | Kaiser et al. |
| 2004/0267164 A1 | 12/2004 | Rhodes et al. |
| 2004/0267265 A1 | 12/2004 | Kyle |
| 2004/0267270 A1 | 12/2004 | Jacobs et al. |
| 2004/0267276 A1 | 12/2004 | Camino et al. |
| 2004/0267277 A1 | 12/2004 | Zannis et al. |
| 2004/0267286 A1 | 12/2004 | Gao et al. |
| 2004/0267304 A1 | 12/2004 | Zannis et al. |
| 2004/0267309 A1 | 12/2004 | Garvin |
| 2004/0267361 A1 | 12/2004 | Donnelly et al. |
| 2004/0267362 A1 | 12/2004 | Hwang et al. |
| 2005/0021087 A1 | 1/2005 | Koseki |
| 2005/0027307 A1 | 2/2005 | Schwartz et al. |
| 2005/0033363 A1 | 2/2005 | Bojarski et al. |
| 2005/0038426 A1 | 2/2005 | Chan |
| 2005/0043805 A1* | 2/2005 | Chudik ............ A61B 17/1684 623/19.14 |
| 2005/0055027 A1 | 3/2005 | Yeung et al. |
| 2005/0055037 A1 | 3/2005 | Fathauer |
| 2005/0064042 A1 | 3/2005 | Vunjak-Novakovic et al. |
| 2005/0065521 A1 | 3/2005 | Steger et al. |
| 2005/0065526 A1 | 3/2005 | Drew et al. |
| 2005/0070906 A1 | 3/2005 | Clark et al. |
| 2005/0070928 A1 | 3/2005 | Heino et al. |
| 2005/0074495 A1 | 4/2005 | Schwartz et al. |
| 2005/0075641 A1* | 4/2005 | Singhatat ............ A61B 17/15 606/86 R |
| 2005/0076478 A1 | 4/2005 | Miyazaki et al. |
| 2005/0085819 A1 | 4/2005 | Ellis et al. |
| 2005/0090828 A1 | 4/2005 | Alford |
| 2005/0090862 A1 | 4/2005 | McDevitt et al. |
| 2005/0096696 A1 | 5/2005 | Forsberg |
| 2005/0096697 A1 | 5/2005 | Forsberg et al. |
| 2005/0096743 A1 | 5/2005 | Schmieding et al. |
| 2005/0101957 A1 | 5/2005 | Buskirk et al. |
| 2005/0107795 A1 | 5/2005 | Morris et al. |
| 2005/0107828 A1 | 5/2005 | Reese |
| 2005/0119531 A1 | 6/2005 | Sharratt |
| 2005/0119696 A1 | 6/2005 | Walters et al. |
| 2005/0124996 A1 | 6/2005 | Hearn |
| 2005/0125031 A1 | 6/2005 | Pipenhagen et al. |
| 2005/0125036 A1 | 6/2005 | Roby |
| 2005/0125073 A1 | 6/2005 | Orban et al. |
| 2005/0131413 A1 | 6/2005 | O'Driscoll et al. |
| 2005/0137600 A1 | 6/2005 | Jacobs et al. |
| 2005/0137624 A1 | 6/2005 | Fallman |
| 2005/0137708 A1* | 6/2005 | Clark ............ A61F 2/38 623/20.15 |

(56) References Cited

U.S. PATENT DOCUMENTS

| | | |
|---|---|---|
| 2005/0149033 A1 | 7/2005 | McGuire et al. |
| 2005/0149122 A1 | 7/2005 | McDevitt et al. |
| 2005/0149187 A1 | 7/2005 | Clark et al. |
| 2005/0159812 A1 | 7/2005 | Dinger et al. |
| 2005/0165416 A1 | 7/2005 | Bojarski et al. |
| 2005/0165482 A1 | 7/2005 | Goldhahn et al. |
| 2005/0171547 A1 | 8/2005 | Aram |
| 2005/0171603 A1 | 8/2005 | Justin et al. |
| 2005/0187565 A1 | 8/2005 | Baker et al. |
| 2005/0187577 A1 | 8/2005 | Selvitelli et al. |
| 2005/0187635 A1 | 8/2005 | Metzger |
| 2005/0203620 A1 | 9/2005 | Steiner et al. |
| 2005/0222618 A1 | 10/2005 | Dreyfuss et al. |
| 2005/0222619 A1 | 10/2005 | Dreyfuss et al. |
| 2005/0228448 A1 | 10/2005 | Li |
| 2005/0240198 A1 | 10/2005 | Albertson et al. |
| 2005/0251159 A1 | 11/2005 | Ewers et al. |
| 2005/0251177 A1 | 11/2005 | Saadat et al. |
| 2005/0251208 A1 | 11/2005 | Elmer et al. |
| 2005/0251210 A1 | 11/2005 | Westra et al. |
| 2005/0267479 A1 | 12/2005 | Morgan et al. |
| 2005/0267533 A1 | 12/2005 | Gertner |
| 2005/0277939 A1 | 12/2005 | Miller |
| 2005/0277961 A1 | 12/2005 | Stone et al. |
| 2005/0283040 A1 | 12/2005 | Greenhalgh |
| 2005/0283156 A1 | 12/2005 | Schmieding et al. |
| 2005/0283158 A1 | 12/2005 | West |
| 2005/0283192 A1 | 12/2005 | Torrie et al. |
| 2006/0004410 A1 | 1/2006 | Nobis et al. |
| 2006/0015103 A1 | 1/2006 | Burke |
| 2006/0015106 A1 | 1/2006 | Lerch et al. |
| 2006/0015107 A1 | 1/2006 | Sklar |
| 2006/0030884 A1 | 2/2006 | Yeung et al. |
| 2006/0030948 A1 | 2/2006 | Manrique et al. |
| 2006/0036265 A1 | 2/2006 | Dant |
| 2006/0052787 A1 | 3/2006 | Re et al. |
| 2006/0052818 A1 | 3/2006 | Drake et al. |
| 2006/0058886 A1* | 3/2006 | Wozencroft ........ A61B 17/1746 623/22.15 |
| 2006/0064125 A1 | 3/2006 | Henderson et al. |
| 2006/0064126 A1 | 3/2006 | Fallin et al. |
| 2006/0069334 A1 | 3/2006 | Moskowitz |
| 2006/0079904 A1 | 4/2006 | Thal |
| 2006/0084943 A1 | 4/2006 | Rosenman et al. |
| 2006/0085000 A1 | 4/2006 | Mohr et al. |
| 2006/0089672 A1 | 4/2006 | Martinek |
| 2006/0095130 A1 | 5/2006 | Caborn et al. |
| 2006/0095131 A1 | 5/2006 | Justin et al. |
| 2006/0100627 A1 | 5/2006 | Stone et al. |
| 2006/0100637 A1 | 5/2006 | Rathbun et al. |
| 2006/0106423 A1 | 5/2006 | Weisel et al. |
| 2006/0111721 A1 | 5/2006 | Puricelli et al. |
| 2006/0116685 A1 | 6/2006 | Urbanski et al. |
| 2006/0121084 A1 | 6/2006 | Borden et al. |
| 2006/0122608 A1 | 6/2006 | Fallin et al. |
| 2006/0122611 A1 | 6/2006 | Morales et al. |
| 2006/0135958 A1 | 6/2006 | Marissen et al. |
| 2006/0149258 A1 | 7/2006 | Sousa |
| 2006/0149266 A1 | 7/2006 | Cordasco |
| 2006/0155287 A1 | 7/2006 | Montgomery et al. |
| 2006/0155328 A1 | 7/2006 | Foerster |
| 2006/0161161 A1 | 7/2006 | Shifrin et al. |
| 2006/0167458 A1 | 7/2006 | Gabele |
| 2006/0167481 A1 | 7/2006 | Baker et al. |
| 2006/0167482 A1 | 7/2006 | Swain et al. |
| 2006/0173492 A1 | 8/2006 | Akerfeldt et al. |
| 2006/0178680 A1 | 8/2006 | Nelson et al. |
| 2006/0189993 A1 | 8/2006 | Stone |
| 2006/0190042 A1 | 8/2006 | Stone et al. |
| 2006/0192319 A1* | 8/2006 | Solar ........................ 264/271.1 |
| 2006/0195101 A1 | 8/2006 | Stevens |
| 2006/0200235 A1 | 9/2006 | Bianchi et al. |
| 2006/0212055 A1 | 9/2006 | Karabey et al. |
| 2006/0229671 A1 | 10/2006 | Steiner et al. |
| 2006/0235407 A1 | 10/2006 | Wang et al. |
| 2006/0235413 A1 | 10/2006 | Denham et al. |
| 2006/0241624 A1 | 10/2006 | Kizuka et al. |
| 2006/0247642 A1 | 11/2006 | Stone et al. |
| 2006/0253130 A1 | 11/2006 | Wolniewicz |
| 2006/0259048 A1 | 11/2006 | Koseki |
| 2006/0271192 A1 | 11/2006 | Olsen et al. |
| 2006/0276793 A1 | 12/2006 | Berry |
| 2006/0276809 A1 | 12/2006 | Oliveira |
| 2006/0276841 A1 | 12/2006 | Barbieri et al. |
| 2006/0276896 A1 | 12/2006 | Fallin et al. |
| 2006/0280768 A1 | 12/2006 | Hwang et al. |
| 2006/0282082 A1 | 12/2006 | Fanton et al. |
| 2006/0282083 A1 | 12/2006 | Fanton et al. |
| 2006/0282085 A1 | 12/2006 | Stone et al. |
| 2006/0293709 A1 | 12/2006 | Bojarski et al. |
| 2007/0005080 A1 | 1/2007 | Wolniewicz et al. |
| 2007/0010857 A1 | 1/2007 | Sugimoto et al. |
| 2007/0016305 A1 | 1/2007 | Chudik |
| 2007/0021779 A1 | 1/2007 | Garvin et al. |
| 2007/0027476 A1 | 2/2007 | Harris et al. |
| 2007/0032800 A1 | 2/2007 | Ortiz et al. |
| 2007/0038218 A1 | 2/2007 | Grevious |
| 2007/0043371 A1 | 2/2007 | Teague et al. |
| 2007/0055249 A1 | 3/2007 | Jensen et al. |
| 2007/0055251 A1 | 3/2007 | Huebner et al. |
| 2007/0055255 A1 | 3/2007 | Siegel |
| 2007/0060922 A1 | 3/2007 | Dreyfuss |
| 2007/0067025 A1 | 3/2007 | Schwartz |
| 2007/0073307 A1 | 3/2007 | Scribner et al. |
| 2007/0073319 A1 | 3/2007 | Mikkaichi et al. |
| 2007/0073322 A1 | 3/2007 | Mikkaichi et al. |
| 2007/0078435 A1 | 4/2007 | Stone et al. |
| 2007/0083236 A1 | 4/2007 | Sikora et al. |
| 2007/0093847 A1 | 4/2007 | Scribner et al. |
| 2007/0100350 A1 | 5/2007 | Deffenbaugh et al. |
| 2007/0112384 A1 | 5/2007 | Conlon et al. |
| 2007/0118217 A1 | 5/2007 | Brulez et al. |
| 2007/0123883 A1 | 5/2007 | Ellis et al. |
| 2007/0142838 A1 | 6/2007 | Jordan |
| 2007/0156174 A1 | 7/2007 | Kaiser et al. |
| 2007/0162018 A1 | 7/2007 | Jensen et al. |
| 2007/0185488 A1 | 8/2007 | Pohjonen et al. |
| 2007/0185532 A1 | 8/2007 | Stone et al. |
| 2007/0185568 A1 | 8/2007 | Schwartz |
| 2007/0191849 A1 | 8/2007 | ElAttrache et al. |
| 2007/0191853 A1 | 8/2007 | Stone |
| 2007/0198036 A1 | 8/2007 | Sklar et al. |
| 2007/0219558 A1 | 9/2007 | Deutsch |
| 2007/0225719 A1 | 9/2007 | Stone et al. |
| 2007/0225805 A1 | 9/2007 | Schmieding |
| 2007/0233241 A1 | 10/2007 | Graf et al. |
| 2007/0239209 A1 | 10/2007 | Fallman |
| 2007/0239275 A1 | 10/2007 | Willobee |
| 2007/0250059 A1 | 10/2007 | Weisshaupt et al. |
| 2007/0250163 A1 | 10/2007 | Cassani |
| 2007/0250175 A1* | 10/2007 | Meridew ............ A61F 2/30734 623/22.21 |
| 2007/0260251 A1 | 11/2007 | Weier et al. |
| 2007/0260279 A1 | 11/2007 | Hotter et al. |
| 2007/0270856 A1 | 11/2007 | Morales et al. |
| 2007/0270878 A1 | 11/2007 | Leisinger |
| 2007/0276387 A1 | 11/2007 | Morales et al. |
| 2007/0276395 A1* | 11/2007 | Burn ................ A61B 17/0483 606/80 |
| 2008/0027430 A1 | 1/2008 | Montgomery et al. |
| 2008/0027446 A1 | 1/2008 | Stone et al. |
| 2008/0033549 A1 | 2/2008 | Marshall et al. |
| 2008/0046009 A1 | 2/2008 | Albertorio et al. |
| 2008/0051836 A1 | 2/2008 | Foerster et al. |
| 2008/0065114 A1 | 3/2008 | Stone et al. |
| 2008/0071299 A1 | 3/2008 | Allinniemi et al. |
| 2008/0082101 A1 | 4/2008 | Reisberg |
| 2008/0082127 A1 | 4/2008 | Stone et al. |
| 2008/0082128 A1 | 4/2008 | Stone |
| 2008/0097430 A1 | 4/2008 | Bernstein et al. |
| 2008/0114370 A1* | 5/2008 | Schoenefeld ...... A61B 17/1721 606/96 |
| 2008/0114460 A1 | 5/2008 | Willobee et al. |
| 2008/0119892 A1 | 5/2008 | Brailovski et al. |

(56) References Cited

U.S. PATENT DOCUMENTS

| | | |
|---|---|---|
| 2008/0132753 A1 | 6/2008 | Goddard |
| 2008/0132932 A1 | 6/2008 | Hoeppner et al. |
| 2008/0132948 A1 | 6/2008 | Surti et al. |
| 2008/0133007 A1 | 6/2008 | Donnelly et al. |
| 2008/0140092 A1 | 6/2008 | Stone et al. |
| 2008/0140093 A1 | 6/2008 | Stone et al. |
| 2008/0140128 A1 | 6/2008 | Smisson et al. |
| 2008/0154260 A1 | 6/2008 | Hoof |
| 2008/0154314 A1 | 6/2008 | McDevitt |
| 2008/0161806 A1 | 7/2008 | Donnelly et al. |
| 2008/0161816 A1* | 7/2008 | Stevens .............. A61B 17/1728 606/87 |
| 2008/0161852 A1 | 7/2008 | Kaiser et al. |
| 2008/0161861 A1 | 7/2008 | Huebner |
| 2008/0161864 A1 | 7/2008 | Beck et al. |
| 2008/0172097 A1 | 7/2008 | Lerch et al. |
| 2008/0183290 A1 | 7/2008 | Baird et al. |
| 2008/0188933 A1 | 8/2008 | Koob et al. |
| 2008/0188936 A1 | 8/2008 | Ball et al. |
| 2008/0221527 A1 | 9/2008 | Bradley et al. |
| 2008/0221578 A1 | 9/2008 | Zeitani |
| 2008/0228186 A1 | 9/2008 | Gall et al. |
| 2008/0234730 A1 | 9/2008 | Cotton et al. |
| 2008/0255613 A1 | 10/2008 | Kaiser et al. |
| 2008/0257363 A1 | 10/2008 | Schoenefeld et al. |
| 2008/0262544 A1 | 10/2008 | Burkhart |
| 2008/0268064 A1 | 10/2008 | Woodell-May |
| 2008/0269674 A1 | 10/2008 | Stone |
| 2008/0275477 A1 | 11/2008 | Sterrett et al. |
| 2008/0300611 A1 | 12/2008 | Houser et al. |
| 2008/0312689 A1 | 12/2008 | Denham et al. |
| 2009/0018589 A1 | 1/2009 | Smisson, III et al. |
| 2009/0018655 A1 | 1/2009 | Brunelle et al. |
| 2009/0043342 A1 | 2/2009 | Freedland |
| 2009/0054928 A1 | 2/2009 | Denham et al. |
| 2009/0062854 A1 | 3/2009 | Kaiser et al. |
| 2009/0082790 A1 | 3/2009 | Shad et al. |
| 2009/0082805 A1 | 3/2009 | Kaiser et al. |
| 2009/0099598 A1 | 4/2009 | McDevitt et al. |
| 2009/0105717 A1 | 4/2009 | Bluechel |
| 2009/0105754 A1 | 4/2009 | Sethi |
| 2009/0118774 A1 | 5/2009 | Miller, III |
| 2009/0118775 A1 | 5/2009 | Burke |
| 2009/0125073 A1 | 5/2009 | Rehm |
| 2009/0138002 A1 | 5/2009 | Fenton |
| 2009/0138054 A1 | 5/2009 | Teague et al. |
| 2009/0156997 A1 | 6/2009 | Trenhaile |
| 2009/0163949 A1 | 6/2009 | Rolnick et al. |
| 2009/0177233 A1 | 7/2009 | Malek |
| 2009/0187244 A1* | 7/2009 | Dross .............. A61F 2/0805 623/13.14 |
| 2009/0192468 A1 | 7/2009 | Stone |
| 2009/0198277 A1 | 8/2009 | Gordon et al. |
| 2009/0204146 A1 | 8/2009 | Kaiser et al. |
| 2009/0228042 A1 | 9/2009 | Koogle, Jr. et al. |
| 2009/0234357 A1 | 9/2009 | Morales et al. |
| 2009/0234358 A1 | 9/2009 | Morales et al. |
| 2009/0240251 A1 | 9/2009 | Gabele |
| 2009/0240335 A1 | 9/2009 | Arcenio et al. |
| 2009/0248091 A1 | 10/2009 | Teague et al. |
| 2009/0265014 A1 | 10/2009 | May et al. |
| 2009/0287215 A1 | 11/2009 | Fisher et al. |
| 2009/0299409 A1 | 12/2009 | Coe et al. |
| 2009/0306711 A1 | 12/2009 | Stone et al. |
| 2009/0312776 A1 | 12/2009 | Kaiser et al. |
| 2009/0318960 A1 | 12/2009 | Burkhart |
| 2009/0318961 A1 | 12/2009 | Stone et al. |
| 2010/0042114 A1 | 2/2010 | Schaffhausen |
| 2010/0087857 A1 | 4/2010 | Stone et al. |
| 2010/0145351 A1* | 6/2010 | Ashman .............. A61B 17/1796 606/96 |
| 2010/0145384 A1 | 6/2010 | Stone et al. |
| 2010/0152752 A1* | 6/2010 | Denove .............. A61B 17/06066 606/148 |
| 2010/0191342 A1 | 7/2010 | Byrd et al. |
| 2010/0211071 A1 | 8/2010 | Lettmann et al. |
| 2010/0211075 A1 | 8/2010 | Stone |
| 2010/0256677 A1 | 10/2010 | Albertorio et al. |
| 2010/0268273 A1 | 10/2010 | Albertorio et al. |
| 2010/0268275 A1 | 10/2010 | Stone et al. |
| 2010/0270306 A1 | 10/2010 | Shiffer |
| 2010/0292743 A1* | 11/2010 | Singhal .............. A61B 17/175 606/86 R |
| 2010/0292792 A1 | 11/2010 | Stone et al. |
| 2010/0305698 A1 | 12/2010 | Metzger et al. |
| 2010/0305709 A1 | 12/2010 | Metzger et al. |
| 2010/0312341 A1 | 12/2010 | Kaiser et al. |
| 2011/0009885 A1 | 1/2011 | Graf et al. |
| 2011/0022083 A1 | 1/2011 | DiMatteo et al. |
| 2011/0026141 A1 | 2/2011 | Barrows |
| 2011/0046733 A1 | 2/2011 | Eggli |
| 2011/0087284 A1 | 4/2011 | Stone et al. |
| 2011/0098727 A1 | 4/2011 | Kaiser et al. |
| 2011/0106153 A1 | 5/2011 | Stone et al. |
| 2011/0112537 A1 | 5/2011 | Bernstein et al. |
| 2011/0112538 A1* | 5/2011 | Dell'Oca .............. A61B 17/82 606/74 |
| 2011/0160767 A1 | 6/2011 | Stone et al. |
| 2011/0160768 A1 | 6/2011 | Stone et al. |
| 2011/0208239 A1 | 8/2011 | Stone et al. |
| 2011/0208240 A1 | 8/2011 | Stone et al. |
| 2011/0213416 A1 | 9/2011 | Kaiser |
| 2011/0218625 A1 | 9/2011 | Berelsman et al. |
| 2011/0224799 A1 | 9/2011 | Stone |
| 2011/0245868 A1 | 10/2011 | Teeslink et al. |
| 2011/0264141 A1 | 10/2011 | Denham et al. |
| 2011/0270278 A1 | 11/2011 | Overes et al. |
| 2011/0270306 A1 | 11/2011 | Denham et al. |
| 2011/0282350 A1* | 11/2011 | Kowarsch .......... A61B 17/1714 606/96 |
| 2012/0004669 A1 | 1/2012 | Overes et al. |
| 2012/0041485 A1 | 2/2012 | Kaiser et al. |
| 2012/0041486 A1 | 2/2012 | Stone et al. |
| 2012/0046693 A1 | 2/2012 | Denham et al. |
| 2012/0053630 A1 | 3/2012 | Denham et al. |
| 2012/0059417 A1 | 3/2012 | Norton et al. |
| 2012/0059418 A1 | 3/2012 | Denham et al. |
| 2012/0089193 A1 | 4/2012 | Stone et al. |
| 2012/0095470 A1 | 4/2012 | Kaiser et al. |
| 2012/0109156 A1 | 5/2012 | Overes et al. |
| 2012/0116409 A1 | 5/2012 | Stone |
| 2012/0116450 A1 | 5/2012 | McDevitt et al. |
| 2012/0116452 A1 | 5/2012 | Stone et al. |
| 2012/0123447 A1 | 5/2012 | Corrao et al. |
| 2012/0123474 A1 | 5/2012 | Zajac et al. |
| 2012/0123541 A1 | 5/2012 | Albertorio et al. |
| 2012/0143215 A1 | 6/2012 | Corrao et al. |
| 2012/0150223 A1 | 6/2012 | Manos et al. |
| 2012/0150297 A1 | 6/2012 | Denham et al. |
| 2012/0165866 A1 | 6/2012 | Kaiser et al. |
| 2012/0165867 A1 | 6/2012 | Denham et al. |
| 2012/0165938 A1 | 6/2012 | Denham et al. |
| 2012/0197271 A1 | 8/2012 | Astorino et al. |
| 2012/0215257 A1 | 8/2012 | McDevitt et al. |
| 2012/0245585 A1 | 9/2012 | Kaiser et al. |
| 2012/0265205 A1* | 10/2012 | Steiner .............. A61B 17/1764 606/80 |
| 2012/0271424 A1* | 10/2012 | Crawford .......... A61B 17/1631 623/17.16 |
| 2012/0290004 A1 | 11/2012 | Lombardo et al. |
| 2012/0296427 A1 | 11/2012 | Conner et al. |
| 2012/0310245 A1 | 12/2012 | Hoeppner et al. |
| 2013/0018375 A1 | 1/2013 | Dell'Oca |
| 2013/0018416 A1 | 1/2013 | Lombardo et al. |
| 2013/0023928 A1 | 1/2013 | Dreyfuss |
| 2013/0023929 A1 | 1/2013 | Sullivan et al. |
| 2013/0023930 A1 | 1/2013 | Stone et al. |
| 2013/0035698 A1 | 2/2013 | Stone et al. |
| 2013/0035722 A1 | 2/2013 | McDevitt et al. |
| 2013/0046341 A1 | 2/2013 | Stone et al. |
| 2013/0103082 A1 | 4/2013 | Kaiser et al. |
| 2013/0110165 A1 | 5/2013 | Burkhart et al. |
| 2013/0110251 A1 | 5/2013 | Metzger et al. |
| 2013/0116730 A1 | 5/2013 | Denham et al. |

(56) References Cited

U.S. PATENT DOCUMENTS

| | | |
|---|---|---|
| 2013/0123810 A1 | 5/2013 | Brown et al. |
| 2013/0123813 A1 | 5/2013 | Stone et al. |
| 2013/0131722 A1 | 5/2013 | Marchand et al. |
| 2013/0138123 A1 | 5/2013 | Stone et al. |
| 2013/0144337 A1 | 6/2013 | Stone et al. |
| 2013/0144338 A1 | 6/2013 | Stone et al. |
| 2013/0158601 A1 | 6/2013 | Stone et al. |
| 2013/0190818 A1 | 7/2013 | Norton |
| 2013/0190819 A1 | 7/2013 | Norton |
| 2013/0204276 A1 | 8/2013 | Stone et al. |
| 2013/0211452 A1 | 8/2013 | Stone et al. |
| 2013/0237997 A1 | 9/2013 | Arai et al. |
| 2013/0245761 A1 | 9/2013 | Conner et al. |
| 2013/0274812 A1 | 10/2013 | Dell'Oca |
| 2013/0289564 A1 | 10/2013 | Bernstein et al. |
| 2013/0317621 A1 | 11/2013 | Metzger et al. |
| 2013/0331848 A1 | 12/2013 | Kaiser et al. |
| 2014/0046367 A1 | 2/2014 | Stone et al. |
| 2014/0046368 A1 | 2/2014 | Kaiser et al. |
| 2014/0067081 A1 | 3/2014 | Stone |
| 2014/0088655 A1 | 3/2014 | Stone et al. |
| 2014/0094913 A1 | 4/2014 | Berelsman et al. |
| 2014/0135835 A1 | 5/2014 | Stone et al. |
| 2014/0163613 A1 | 6/2014 | Stone et al. |
| 2014/0163614 A1 | 6/2014 | Denham et al. |
| 2014/0194927 A1 | 7/2014 | Kaiser et al. |
| 2014/0200583 A1 | 7/2014 | Stone et al. |
| 2014/0257378 A1 | 9/2014 | Norton et al. |
| 2014/0276992 A1 | 9/2014 | Stone et al. |
| 2014/0277447 A1 | 9/2014 | Berelsman et al. |
| 2014/0324101 A1 | 10/2014 | Denham et al. |
| 2014/0330311 A1 | 11/2014 | Denham et al. |
| 2014/0350674 A1 | 11/2014 | Stone et al. |
| 2015/0012094 A1 | 1/2015 | Denham et al. |
| 2015/0057757 A1 | 2/2015 | Metzger et al. |

FOREIGN PATENT DOCUMENTS

| | | |
|---|---|---|
| AU | 5850469 | 1/1971 |
| AU | 5963869 | 2/1971 |
| AU | 1505470 | 11/1971 |
| AU | 2223767 | 5/1973 |
| AU | 3615171 | 5/1973 |
| AU | 5028569 | 9/1973 |
| AU | 7110887 | 10/1987 |
| AU | 639410 | 11/1989 |
| AU | 651929 | 8/1994 |
| DE | 2529669 | 3/1976 |
| DE | 2747312 | 4/1979 |
| DE | 2818254 | 10/1979 |
| DE | 2919009 | 11/1979 |
| DE | 3027138 | 12/1981 |
| DE | 3225620 | 2/1983 |
| DE | 3136083 | 3/1983 |
| DE | 233303 C | 2/1986 |
| DE | 4127550 | 2/1993 |
| DE | 4302397 | 7/1993 |
| DE | 29621340 | 5/1998 |
| DE | 19841252 | 3/2000 |
| DE | 20207781 U1 | 8/2002 |
| EP | 19062 A1 | 11/1980 |
| EP | 0108912 | 5/1984 |
| EP | 0129422 | 12/1984 |
| EP | 0129442 | 12/1984 |
| EP | 0172130 | 2/1986 |
| EP | 0241240 | 10/1987 |
| EP | 0241792 | 10/1987 |
| EP | 0260970 | 3/1988 |
| EP | 0270704 | 6/1988 |
| EP | 0282789 | 9/1988 |
| EP | 0315371 | 5/1989 |
| EP | 0317406 | 5/1989 |
| EP | 0340159 | 11/1989 |
| EP | 0346183 | 12/1989 |
| EP | 0349173 | 1/1990 |
| EP | 0374088 | 6/1990 |
| EP | 0409364 | 1/1991 |
| EP | 0415915 | 3/1991 |
| EP | 0440991 | 8/1991 |
| EP | 0441065 | 8/1991 |
| EP | 0451932 | 10/1991 |
| EP | 0464480 | 1/1992 |
| EP | 0490417 | 6/1992 |
| EP | 0497079 | 8/1992 |
| EP | 0502509 | 9/1992 |
| EP | 0502698 | 9/1992 |
| EP | 520177 | 12/1992 |
| EP | 0546726 | 6/1993 |
| EP | 0574707 | 12/1993 |
| EP | 0582514 | 2/1994 |
| EP | 0591991 | 4/1994 |
| EP | 0598219 | 5/1994 |
| EP | 0611551 A1 | 8/1994 |
| EP | 0627203 | 12/1994 |
| EP | 0651979 | 5/1995 |
| EP | 0669110 | 8/1995 |
| EP | 0686373 | 12/1995 |
| EP | 0702933 | 3/1996 |
| EP | 0775473 | 5/1997 |
| EP | 0913123 | 5/1999 |
| EP | 0913131 | 5/1999 |
| EP | 99121106 | 10/1999 |
| EP | 991210527 | 10/1999 |
| EP | 0995409 | 4/2000 |
| EP | 1013229 | 6/2000 |
| EP | 1093773 | 4/2001 |
| EP | 1093774 | 4/2001 |
| EP | 1555945 | 7/2005 |
| EP | 2238944 A2 | 10/2010 |
| EP | 2544607 A1 | 1/2013 |
| EP | 2709557 A1 | 3/2014 |
| FR | 2622790 | 5/1989 |
| FR | 2655840 | 6/1991 |
| FR | 2682867 | 4/1993 |
| FR | 2687911 | 9/1993 |
| FR | 2688689 | 9/1993 |
| FR | 2704140 | 10/1994 |
| FR | 2717070 | 9/1995 |
| FR | 2723528 | 2/1996 |
| FR | 2744010 | 8/1997 |
| FR | 2745999 | 9/1997 |
| FR | 2770764 | 5/1999 |
| GB | 401677 | 11/1933 |
| GB | 1413477 | 11/1975 |
| GB | 1485681 | 9/1977 |
| GB | 2083751 | 3/1982 |
| GB | 2118474 | 11/1983 |
| GB | 2227175 | 7/1990 |
| GB | 2253147 A | 9/1992 |
| GB | 2312376 | 10/1997 |
| GB | 2403416 A | 1/2005 |
| JP | 5362911 | 5/1978 |
| JP | 5362912 | 5/1978 |
| JP | 5374942 | 6/1978 |
| JP | 5378230 | 6/1978 |
| JP | 62159647 | 7/1987 |
| JP | 62295657 | 12/1987 |
| JP | 5269160 | 10/1993 |
| JP | 5300917 | 11/1993 |
| JP | 751292 | 2/1995 |
| JP | 10211213 | 8/1998 |
| WO | WO-8300615 | 3/1983 |
| WO | WO-8603666 | 7/1986 |
| WO | WO-8701270 | 3/1987 |
| WO | WO-8901767 | 3/1989 |
| WO | WO-8909030 | 10/1989 |
| WO | WO-8910096 | 11/1989 |
| WO | WO-9008510 | 8/1990 |
| WO | WO-9203980 | 3/1992 |
| WO | WO-9314705 | 8/1993 |
| WO | WO-9315694 | 8/1993 |
| WO | WO-9502373 | 1/1995 |
| WO | WO-9503003 | 2/1995 |
| WO | WO-9529637 | 11/1995 |

(56) References Cited

FOREIGN PATENT DOCUMENTS

| WO | WO-9532670 | 12/1995 |
|---|---|---|
| WO | WO-9609797 A1 | 4/1996 |
| WO | WO-9629029 | 9/1996 |
| WO | WO-9737603 | 10/1997 |
| WO | WO-9812991 | 4/1998 |
| WO | WO-9812992 | 4/1998 |
| WO | WO-9822047 | 5/1998 |
| WO | WO-9822048 | 5/1998 |
| WO | WO-9901084 | 1/1999 |
| WO | WO-9912480 | 3/1999 |
| WO | WO-9937219 A1 | 7/1999 |
| WO | WO-9944544 | 9/1999 |
| WO | WO-9952472 A1 | 10/1999 |
| WO | WO-0040159 | 7/2000 |
| WO | WO-0139671 | 6/2001 |
| WO | WO-0236020 | 5/2002 |
| WO | WO-03005914 A1 | 1/2003 |
| WO | WO-03071962 | 9/2003 |
| WO | WO-03077772 | 9/2003 |
| WO | WO-03092551 A1 | 11/2003 |
| WO | WO-2004091412 A1 | 10/2004 |
| WO | WO-2005104992 A1 | 11/2005 |
| WO | WO-2005122954 A1 | 12/2005 |
| WO | WO-2006023661 A2 | 3/2006 |
| WO | WO-2006055823 A2 | 5/2006 |
| WO | WO-2007045460 A2 | 4/2007 |
| WO | WO-2007103562 A2 | 9/2007 |
| WO | WO-2007109280 A2 | 9/2007 |
| WO | WO-2008002550 A2 | 1/2008 |
| WO | WO-2008015171 A1 | 2/2008 |
| WO | WO-2008073588 A2 | 6/2008 |
| WO | WO-2009012021 A1 | 1/2009 |
| WO | WO-2011112371 A1 | 9/2011 |
| WO | WO-2011150238 A1 | 12/2011 |
| WO | WO-2012134999 A1 | 10/2012 |
| WO | WO-2012158583 A1 | 11/2012 |
| WO | WO-2013066974 A1 | 5/2013 |
| WO | WO-2013074525 A1 | 5/2013 |
| WO | WO-2014/100109 A1 | 6/2014 |
| WO | WO-2014151766 A1 | 9/2014 |

OTHER PUBLICATIONS

International Preliminary Report on Patentability and Written Opinion mailed Nov. 28, 2013 for PCT/US2012/037703, which claims benefit of U.S. Appl. No. 13/109,672, filed May 17, 2011,and U.S. Appl. No. 13/109,667, filed May 17, 2011.
"ToggleLoc™ Fixation Device with ZipLoop™ Technology: ACL Reconstruction Bone-Tendon-Bone," by James R. Andrews, M.D., of Biomet Sports Medicine, a Biomet Company Brochure (2013), pp. 1-20.
International Preliminary Report on Patentability and Written Opinion mailed May 30, 2014 for PCT/US2012/064832 which claims benefit of U.S. Appl. No. 13/295,126, filed Nov. 14, 2011.
International Search Report and Written Opinion mailed Jun. 6, 2014 for PCT/US2014/026413 which claims benefit of U.S. Appl. No. 14/095,614, filed Dec. 3, 2013 and U.S. Appl. No. 14/095,639, filed Dec. 3, 2013.
ToggleLoc Fixation Device with ZipLoop Technology: Biceps Tendon Reattachment by Mark J. Albritton, M.D. and Daniel Worrel, M.D. of Biomet Sports Medicine, a Biomet Company Brochure (2099, 2011), pp. 1-12.
International Search Report and Written Opinion mailed Mar. 6, 2014 for PCT/US2013/075989 which claims benefit of U.S. Appl. No. 13/720,648, filed Dec. 19, 2012.
"AperFix® System Surgical Technique Guide. Single Tunnel Double Bundle.™" Cayenne Medical brochure. (Aug. 2008) 8 sheets.
"Arthroscopic Meniscal Repair using the Meniscal Cinch™", Surgical Technique brochure. (2008) Arthrex® 6 sheets.
"Bio-Intrafix (TCP/PLA & Intrafix, Tibial Soft Tissue Fasteners," by DePuy Mitek, 6 sheets, (date unknown).
"Bio-Intrafix Tibial Soft Tissue Fasteners, Building on the Legacy of IntraFix," brochure. DePuy Mitek,(Feb. 2007) 6 sheets.
"Biomechanical Evaluation of the Biomet Sports Medicine JurggerKnot™ Soft Anchor in Porcine Bone," Study completed Jan. 2010. Biomet Sports Medicine Research and Development, Warsaw, Indiana. 2 pages.
"Do your next distal tendon repair with . . . The Lubbers Technique", Teno Fix® brochure, 2003 (2 pages) Ortheon® Medical.
"EZ Loc Femoral Fixation Device," copyright 2005 Arthrotek, Inc. (8 sheets).
"JuggerKnot™ Soft Anchor Midfoot Repair," brochure. Biomet Sports Medicine (Jul. 2011) 12 sheets.
"JuggerKnot™ Soft Anchor. It's Small. It's strong. And it's all suture . . . " Ordering Information brochure. Biomet Sports Medicine (Jun. 2011) 2 sheets.
"JuggerKnot™ Soft Anchor. Labral Repair," brochure. Biomet Sports Medicine (Apr. 2011) 12 sheets.
"Make your next tendon repair an open-and-shut case. The Teno Fix® Tendon Repair System", Teno Fix® brochure, 2003 (2 pages) Ortheon® Medical.
"PANALOK Anchor with PDS II and ETHIBOND Suture", Mitek Products ETHICON, 1997.
"SE Graft Tensioning System Surgical Technique," Linvatec Corporation copyright 2003, 2004.
"Suture Tensioner w/Tensiometer," Arthrex® , Inc. catalog "Next Generation in Knee Ligament Reconstruction & Repair Technology," 2009.
"Technique for ACL Reconstruction with Acufex Director Drill Guide and Endobutton CL," by Thomas D. Roseberg, copyright 1999 Smith & Nephew.
"TriTis™ Tibial Fixation System and Implant" brochure. Scandius Biomedical (2006).
A. Weiler, et al; Biodegradierbare Interferenzschrauben in der Kreuzbandchirurgie; OP-Journal 14 pp. 278-284; (Mar. 1998).
Arthrotek, A Biomet Company; Knees; Sure fire Hybrid Meniscal Device. (2005).
Arthrotek, A Biomet Company; Sure fire Hybrid Meniscal Device; Launch Date: Fall AANA 2004.
F. Alan Barber, M.D., "Uses and Abuses of Sutures and Anchors," Shoulder Scope, San Diego Shoulder Arthroscopy Library. http://www.shoulder.com/bass_barber.html Printed May 19, 2005.
F. Alan Barber, M.D., "Using Sutures and Anchors," San Diego Shoulder Arthroscopy Course, 17th Annual Meeting. (Jun. 14, 2000).
Flavia Namie Azato, et al. "Traction endurance biomechanical study of metallic suture anchors at different insertion angles," Acta ortop. bras., vol. 11, No. 1, Sao Paulo, Jan./Mar. 2003.
Hecker AT, et al., "Pull-out strength of suture anchors for rotator cuff and Bankart lesion repairs," Am J Sports Med. 1993.
International Preliminary Report on Patentability mailed Dec. 6, 2012 for PCT/US2011/038188 claiming benefit of U.S. Appl. No. 12/788,966, filed May 27, 2010.
International Preliminary Report on Patentability mailed Sep. 20, 2012 for PCT/US2011/026349 which claims benefit of U.S. Appl. No. 12/719,337, filed Mar. 8, 2010.
International Search Report and Written Opinion mailed Feb. 6, 2013 for PCT/US2012/064832 which claims benefit of U.S. Appl. No. 13/295,126, filed Nov. 14, 2011.
International Search Report and Written Opinion mailed Jul. 28, 2011 for PCT/US2011/026349 claiming benefit of U.S. Appl. No. 12/938,902, filed Nov. 3, 2010; and U.S. Appl. No. 12/719,337, filed Mar. 8, 2010.
International Search Report and Written Opinion mailed Mar. 6, 2013 for PCT/US2012/062738 which claims benefit of U.S. Appl. No. 13/288,459, filed Nov. 3, 2011.
International Search Report and Written Opinion mailed Oct. 14, 2011 for PCT/US2011/038188 filed May 26, 2011 claiming benefit of U.S. Appl. No. 12/788,973, filed May 27, 2010 and U.S. Appl. No. 12/788,966, filed May 27, 2010.
International Search Report and Written Opinion mailed Sep. 21, 2012 for PCT/US2012/037703 filed May 14, 2012 claiming benefit of U.S. Appl. No. 13/109,667, filed May 17, 2011 and U.S. Appl. No. 13/109,672, filed May 17, 2011.

(56) References Cited

OTHER PUBLICATIONS

Invitation to Pay Additional Fees mailed Aug. 5, 2011 for PCT/US2011/038188 claiming benefit of U.S. Appl. No. 12/788,973, filed May 27, 2010 and U.S. Appl. No. 12/788,966, filed May 27, 2010.
Invitation to Pay Additional Fees mailed Jul. 19, 2012, for PCT/US2012/037703 claiming benefit of U.S. Appl. No. 13/109,667, filed May 7, 2011.
Invitation to Pay Additional Fees mailed Jun. 9, 2011 for PCT/US2011/026349 claiming benefit of U.S. Appl. No. 12/938,902, filed Nov. 3, 2010; and U.S. Appl. No. 12/719,337, filed Mar. 8, 2010.
Lawhorn, M.D., Keith, MaxFire™ Meniscal Repair Device with Zip Loop™ Technology, Biomet Sports Medicine, Feb. 29, 2008.
Mark D. Miller et al.; "Pitfalls Associated with FasT-Fix Meniscal Repair," Arthroscopy: The Journal of Arthroscopic and Related Surgery, vol. 18, No. 8 Oct. 2002: pp. 939-943.
Opus Medical; The AutoCuff System; www.opusmedical.com; 2003.
Patrick Hunt, et al.; Development of a Perforated Biodegradable Interference Screw; Arthroscopy: The Journal of Arthroscopic and Related Surgery, vol. 21, No. 3; pp. 258-265; Mar. 2005.
Pioneer® Sternal Cable System (2010).
Rapid Sternal Closure (2006) KLS Martin L.P. http://www.rapidsternalclosure.com/medical/demo.php Web accessed Sep. 8, 2008.
Roy Alan Majors, M.D.; "Meniscal repairs: proven techniques and current trends," Lippincott Williams & Wilkins, Inc.; 2002.
Saxena, Pankaj, MCh, DNB et al., "Use of Double Wires in Sternal Closure, A Useful Technique," Texas Heart® Institute. Journal List>Tex Heart Inst J > v.33(4); (2006).
Shoulder Arthroscopy; pp. H-2-H-22. (date unknown).
Smith & Nephew Endoscopy, "Endoscopic Meniscal Repair Using the T-Fix;" 1996.
Smith & Nephew, "Fast-Fix," Meniscal Repair System; 2001.
Stuart E. Fromm, M.D., RapidLoc, Meniscal Repair System, Mitek Products, Ethicon, 2001.
ToggleLoc™ Femoral Fixation Device, Arthrotek, Mar. 31, 2006.
Zeitani, Jacob, M.D., "A New Sternal Reinforcement Device to Prevent and Treat Sternal Dehiscence," CTSNet.org (Jun. 30, 2008).
Ziptight™ Fixation System Featuring Zip Loop™ Technology. Ankle Syndesmosis. Surgical Protocol by Timothy Charlton, M.D. Biomet Sports® Medicine brochure. (Jun. 15, 2011) 8 pages.
US 6,238,418, 05/2001, Schwartz et al. (withdrawn)

* cited by examiner

METHOD AND APPARATUS FOR INTRAOSSEOUS MEMBRANE RECONSTRUCTION

CROSS-REFERENCE TO RELATED APPLICATIONS

The present application is a divisional of U.S. patent application Ser. No. 13/281,016 filed Oct. 25, 2011. The entire disclosure of the above application is incorporated by reference.

FIELD

The present disclosure relates to methods and devices for interosseous membrane reconstruction.

BACKGROUND

This section provides background information related to the present disclosure which is not necessarily prior art.

The interosseous membrane is a broad and thin plane of fibrous connective tissue that separates various different bones of the human body. For example, the long bones of the lower arm and the leg are connected by interosseous membranes. In the arm, an interosseous membrane extends between the radius and ulna to transfer forces from the radius to the ulna and humerus. As the forearm moves from pronation to supination, the interosseous membrane fibers move from a relaxed state to a tense neutral position, and then return to the relaxed state as the forearm enters supination. In the leg, the interosseous membrane extends between the tibia the fibula, running along the crest of each bone. It fulfills many of the same functions in the leg as in the arm.

Tears in the membrane can occur as a result of severe trauma or fracturing of adjacent bone, and may also be created during surgery. To facilitate healing of such tears, pins are often inserted through the bones surrounding the interosseous membrane, such as the radius and the ulna. Use of pins, however, can hinder range of motion, such as pronation and supination of the forearm for example.

SUMMARY

This section provides a general summary of the disclosure, and is not a comprehensive disclosure of its full scope or all of its features.

The present teachings provide for a method for repairing a defect in an interosseous membrane located between a first bone and a second bone. The method includes: coupling a flexible member to the first bone and the second bone, the flexible member extending past a first area of the interosseous membrane between the first bone and the second bone; and orienting the flexible member such that the flexible member extends generally parallel to fibers of the first area of the interosseous membrane.

The present teachings further provide for a method for repairing a defect in an interosseous membrane located between a first bone and a second bone. The method includes: orienting a first suture portion such that the first suture portion extends generally parallel to fibers of a first area of the interosseous membrane; coupling the first suture portion to the first bone and the second bone, the first suture portion extending past a first area of the interosseous membrane between the first bone and the second bone; orienting and coupling a second suture portion to the first bone and the second bone, the second suture portion extending past the first area of the interosseous membrane between the first bone and the second bone.

The present teachings also provide for a kit for repairing a defect in an interosseous membrane located between a first bone and a second bone, the kit includes at least one suture and a first drill guide. The first drill guide includes a body; a bone engagement surface; a first through hole extending through the body, the first through hole defines a first longitudinal axis; and a second through hole extending through the body, the second through hole defines a second longitudinal axis that is angled one of about 20° to about 25° or about 40° to about 45° relative to the first longitudinal axis.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1A:
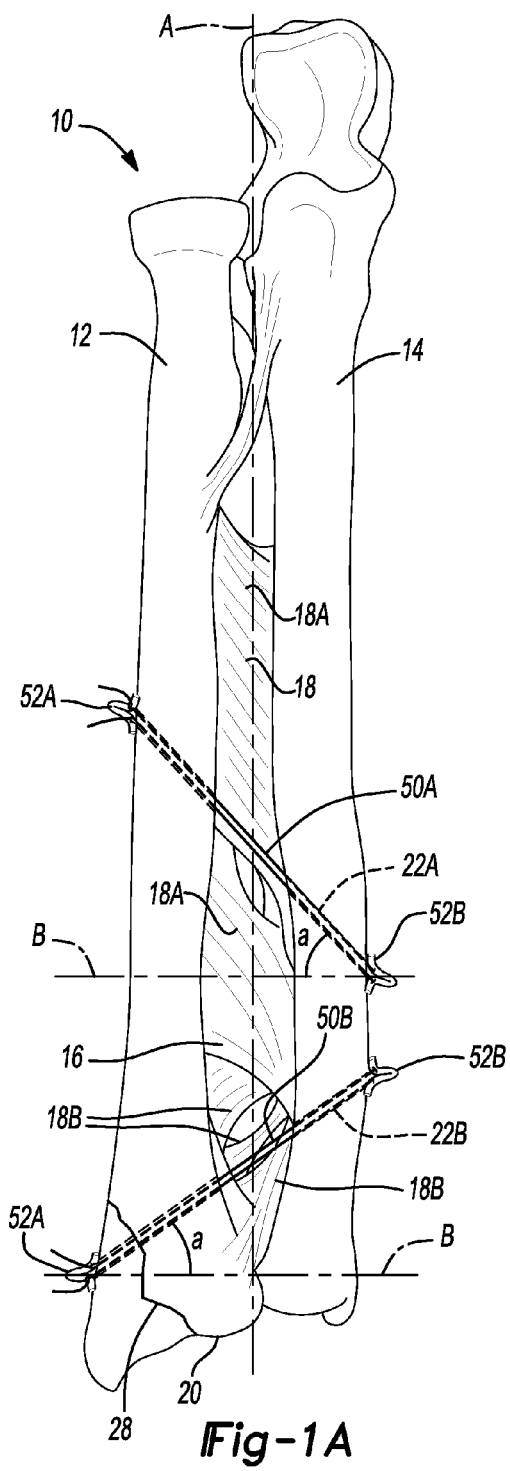
FIG. 1A is an anterior view of a forearm with sutures extending between a radius and ulna of the forearm in accordance with the present teachings.
Figure 1B:
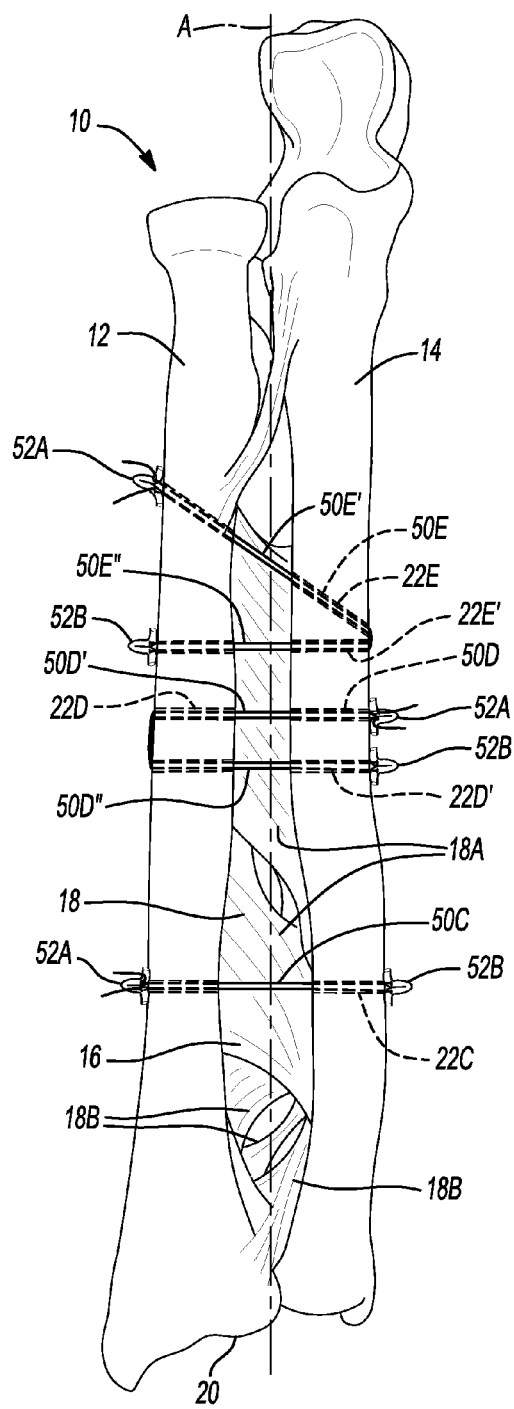
FIG. 1B is an anterior view of additional sutures extending between the radius and the ulna.

FIGS. 1A and 1B illustrate an anterior view of a forearm 10 including a radius 12, an ulna 14, and an interosseous membrane 16 extending between the radius 12 and the ulna 14 and across a longitudinal axis A of the forearm 10. The interosseous membrane 16, for example, connects the radius 12 to the ulna 14, facilitates movement of the forearm 10 from pronation to supination, and transfers forces between the radius 12, the ulna 14, and the humerus (not illustrated). The interosseous membrane 16 includes tissue having a plurality of fibers 18.

A first group of fibers 18A generally extend obliquely across the longitudinal axis A from the radius 12 proximally to the ulna 14 distally. A second group of fibers 18B extend obliquely across the longitudinal axis A from the radius 12 distally to the ulna 14 proximally. The second group of fibers 18B is generally smaller than the first group of fibers 18A and is located between the first group of fibers 18A and a distal end 20 of the forearm 10. One skilled in the art will recognize the various orientations of the fibers 18 and the angle of the fibers 18 with respect to the radius 12 and the ulna 14. One skilled in the art will also recognize that no two interosseous membranes are exactly the same, but that the fibers 18 among different patients are similarly orientated, as generally illustrated in FIGS. 1A and 1B, and as described above.

The radius 12 and the ulna 14 can be further connected by a plurality of flexible members, such as sutures 50, which extend through each of the radius 12, the interosseous membrane 16, and the ulna 14. As further described herein, the sutures 50 can be any suitable suture and can be anchored to the radius 12 and the ulna 14 in any suitable manner, such as with a first anchor 52A at the radius 12 and a second anchor 52B at the ulna 14. The sutures 50 supplement the connection between the radius 12 and the ulna 14 provided by the interosseous membrane 16, such as in instances where the interosseous membrane 16 has been damaged due to trauma or during surgery. This damage can include tears in the interosseous membrane 16 or separation of the interosseous membrane from either the radius 12 or the ulna 14.

The sutures 50 each generally extend through a bore 22 formed through the radius 12, the ulna 14, and the interosseous membrane 16. Each of the sutures 50 are generally positioned and orientated to permit natural movement of the radius 12, the ulna 14, and the interosseous membrane 16. For example and with reference to FIG. 1A, suture 50A is orientated such that it extends generally parallel to the interosseous fibers 18 of the first group of interosseous fibers 18A and across the first group of interosseous fibers 18A between the radius 12 and the ulna 14; and suture 50B is orientated such that it extends generally parallel to the interosseous fibers 18 of the second group of interosseous fibers 18B and across the second group of interosseous fibers 18B between the radius 12 and the ulna 14. The suture 50A and the suture 50B are thus each generally orientated at an angle "a" of from about 5° to about 55°, such as about 20° to about 25° or about 40° to about 45°, relative to a line B extending perpendicular to the longitudinal axis A.

The suture 50A is seated in a first bore 22A and the suture 50B is seated in a second bore 22B. Orienting the sutures 50A and 50B parallel to fibers 18 of the first and the second groups of interosseous fibers 18A and 18B respectively generally permits natural movement of the interosseous membrane 16, such as between pronation and supination of the forearm 10, and allows natural loading between the radius 12 and the ulna 14. Such natural movement and loading is not permitted, but is rather restricted by, use of rigid fixation members, such as rigid pins. To stabilize a bone fracture, such as a fracture 28 of the radius 12, the suture 50B can be orientated such that it extends through the fracture 28.

With additional reference to FIG. 1B, the sutures 50 can be provided at a variety of other orientations as well, in addition to or in place of the orientations of sutures 50A and 50B of FIG. 1A. For example, one or more of the sutures 50 can be orientated so as to extend across the interosseous membrane 16 substantially perpendicular to the longitudinal axis A, such as suture 50C seated in bore 22C. Orienting the suture 50C perpendicular to the longitudinal axis A stabilizes relative movement of the radius 12 and the ulna 14 perpendicular to the longitudinal axis A. In other words, the radius 12 and the ulna 14 are stabilized so that they do not move relative to each other perpendicular to the longitudinal axis A. The suture 50C is anchored at the radius 12 with the first anchor 52A and at the ulna 14 with the second anchor 52B.

Any of the sutures 50 can be implanted such that they loop through the forearm 10 and are anchored to only one of either the radius 12 or the ulna 14. For example, both the first anchor 52A and the second anchor 52B of the suture 50D are mounted to the ulna 14. A first portion 50D' of the suture 50D extends from the first anchor 52A to the radius 12 through a first bore 22D. Upon exiting the first bore 22D at the radius 12, the suture 50D loops back into the radius 12 such that a second portion 50D" extends through the radius 12 to the ulna 14 through a second bore 22D', where the suture 50D is secured by the second anchor 52B. Each of the first bore 22D and the second bore 22D' are extended substantially perpendicular to the longitudinal axis A, and thus the first and second portions 50D' and 50D" of the suture 50D are perpendicular to the longitudinal axis A as well. While the suture 50D is secured to the ulna 14 with the first anchor 52A and the second anchor 52B, the suture 50D can be reversed such that the first anchor 52A and the second anchor 52B are secured to the radius 12. By looping the suture 50D through the forearm 10 as illustrated, the suture 50D can provide additional stability to the radius 12 and the ulna 14 perpendicular to the longitudinal axis A.

As illustrated in FIG. 1B, suture 50E provides another possible orientation for the suture 50. The suture 50E is orientated such that the first anchor 52A and the second anchor 52B are both anchored to the radius 12. A first portion 50E' of the suture 50E extends from the first anchor 52A to the ulna 14 through a first bore 22E. Upon exiting the first bore 22E at the ulna 14, the suture 50E loops back into the ulna 14 such that a second portion 50E" extends through the ulna 14 to the radius 12 through a second bore 22E', where the suture 50E is secured by the second anchor 52B. The first bore 22E is angled such that it extends through the interosseous membrane 16 substantially parallel to the fibers 18 of the first group of interosseous fibers 18A. Thus, the first portion 50E' is also substantially parallel to the fibers 18 of the first group of interosseous fibers 18A. The second bore 22E' is substantially perpendicular to the longitudinal axis A, and thus the second portion 50E" of the suture 50E is perpendicular to the longitudinal axis A. The first portion 50E' is angled about 5° to about 55° relative to the second portion 50E", such as about 20° to about 25° or about 40° to about 45°.

Orienting the second portion 50E" generally perpendicular to the longitudinal axis A stabilizes the radius 12 with respect to the ulna 14 perpendicular to the longitudinal axis A and orienting the first portion 50E' generally parallel to the fibers 18 of the first group of interosseous fibers 18A generally permits natural movement of the radius 12 with respect to the ulna 14, such as during supination and pronation of the forearm 10, and distributes load between the radius 12 and the ulna 14 similar as to how the load would be distributed naturally. Thus, the suture 50E is a dual purpose suture that generally provides two stabilizing effects. First, the first portion 50E' permits load transfer between the radius 12 and the ulna 14 in a manner similar to that which occurs naturally. The second portion 50E" stabilizes the radius 12 and the ulna 14 along the longitudinal axis A so that the radius 12 and the ulna 14 do not move relative to each other perpendicular to the longitudinal axis A.

The forearm 10 can be provided with any combination of the sutures 50A-50E, and is thus not limited to the arrangements illustrated in FIGS. 1A and 1B. For example, each one of the sutures 50A-50E can be included in a single forearm 10. The arrangement of the sutures 50A-50E can be determined by a physician based on, for example, the patient's anatomy, damage to the interosseous membrane 16, and observed orientations of the patient's interosseous fibers 18.

Figure 2:
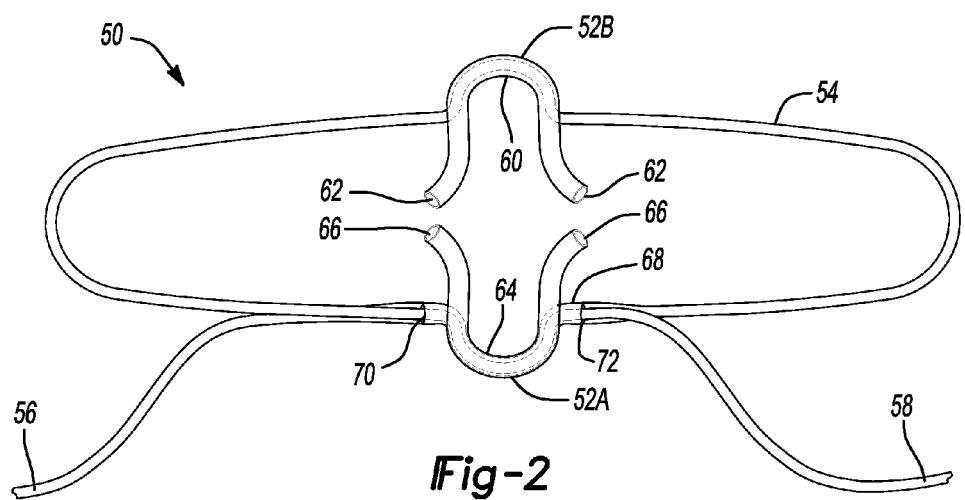
FIG. 2 illustrates an exemplary suture according to the present teachings.

With additional reference to FIG. 2, further details of the suture 50, which generally includes a suture construct or assembly, will be described. The description of the suture 50 generally applies to each of the sutures 50A-50E described above. The suture 50 can generally include a hollow braided suture strand 54 including a first end 56 and a second end 58. The second anchor 52B is approximately equidistant between the first end 56 and the second end 58. The second anchor 52B is generally U-shaped and flexible. The second anchor 52B includes a base 60 and a pair of feet 62, which extend from the base 60. The base 60 is connected to the suture strand 54 in any suitable manner, and may be integral with the suture strand 54 as illustrated.

The first anchor 52A is between the first end 56 of the suture strand 54 and the second anchor 52B. The first anchor 52A includes a base 64 and a pair of feet 66. Integral with the base 64 and the suture strand 54 is a sleeve portion 68 of the suture 54 that includes a first opening 70 and a second opening 72 between braided fibers that is opposite to the first opening 70. The second end 58 of the suture strand 54 is inserted through the sleeve 68 such that the suture strand 54 enters the sleeve 68 through the first opening 70 and exits the sleeve 68 through the second opening 72.

The suture 50 is a knotless, self-locking suture. As the first and second ends 56 and 58 are pulled, friction between the interior of the sleeve 68 and the portion of the suture strand 54 located within the sleeve 68 causes the suture 50 to "automatically" lock in a reduced size or diameter configuration in which tension is maintained without use of a knot. The suture 50 is similar to the self-locking suture construct 300A of FIG. 15 of U.S. application Ser. No. 12/915,962 filed on Oct. 29, 2010, titled Method and Apparatus for Securing Soft Tissue to Bone, and assigned to Biomet Sports Medicine, LLC, the disclosure of which is incorporated herein by reference. Additional description of the suture 50 is thus included in U.S. application Ser. No. 12/915,962. Additional sutures that can be used in accordance with the present teachings include those disclosed in U.S. Pat. No. 7,658,751, which issued on Feb. 9, 2010 and is assigned to Biomet Sports Medicine, LLC, Warsaw, Ind. The disclosure of U.S. Pat. No. 7,658,751 is incorporated herein by reference.

Figure 3:
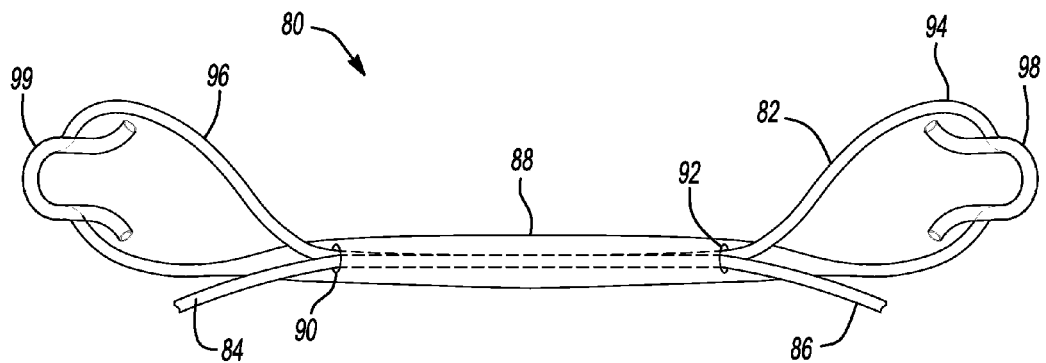
FIG. 3 illustrates another suture according to the present teachings.

The suture 50 can be replaced with any suitable biocompatible fastening device that will permit natural movement of the interosseous membrane 16. For example and with reference to FIG. 3, a suture 80 can be used. The suture 80 is a self-locking suture that includes a hollow, braided suture strand 82 with a first end 84 and a second end 86. A sleeve portion 88 of the suture 80 is located about halfway between the first end 84 and the second end 86. The sleeve 88 includes a first opening 90 and a second opening 92 between braided fibers. The first end 84 is inserted into the sleeve 88 through the second opening 92 and passed through the sleeve 88 such that the first end 84 extends out through the first opening 90 of the sleeve 88. The second end 86 is inserted into the sleeve 88 through the first opening 90 and passed through the sleeve 88 such that the second end 86 extends out through the second opening 92 of the sleeve 88. Inserting the first and the second ends 84 and 86 through the sleeve 88 causes the suture strand 82 to form a first loop 94 including a first anchor 98 and a second loop 96 including a second anchor 99. As the first end 84 and the second end 86 are pulled through the sleeve 88, friction in the sleeve 88 causes the suture 80 to "automatically" lock in a reduced size or diameter configuration in which tension is maintained without use of a knot. The suture 80 is similar to the self-locking suture construct 250 of FIG. 13 of U.S. application Ser. No. 12/915,962, the disclosure of which has been incorporated herein by reference. Additional description of the suture 80 is thus included in U.S. application Ser. No. 12/915,962.

In addition to the sutures and suture constructs described herein and incorporated herein by reference, any other suitable suture, suture construct, knit, or flexible member, such as a Nitinol strand, can be inserted in the bores 22 to connect the radius 12 and ulna 14 in a manner that will transfer loads between the radius 12 and ulna 14, provide at least near natural range of motion between the radius 12 and ulna 14, and stabilize the radius 12 and ulna 14 along the longitudinal axis A such that neither the radius 12 nor the ulna 14 move relative to each other perpendicular to the longitudinal axis A.

Figure 4:
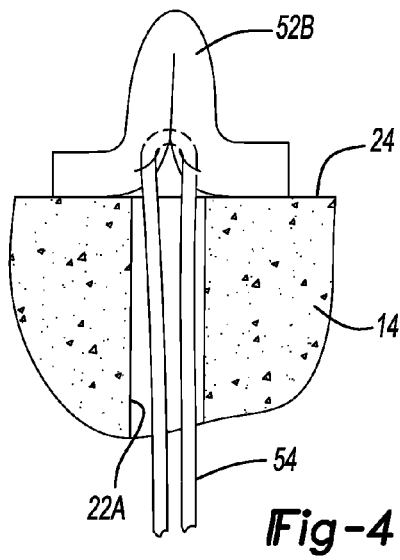
FIG. 4 illustrates an end of the suture of FIG. 2 anchored at an exterior of a bone of the forearm.

The anchors 52A, 52B, 98, and 99 are all configured to expand when compressed against bone so as to anchor to an exterior of the bone. For example and with reference to FIG. 4, as the suture strand 54 is pulled away from an outer surface 24 of the ulna 14 through the first bore 22A, the second anchor 52B compresses against the outer surface 24 and expands to anchor the suture 50 to the ulna 14.

Figure 5:
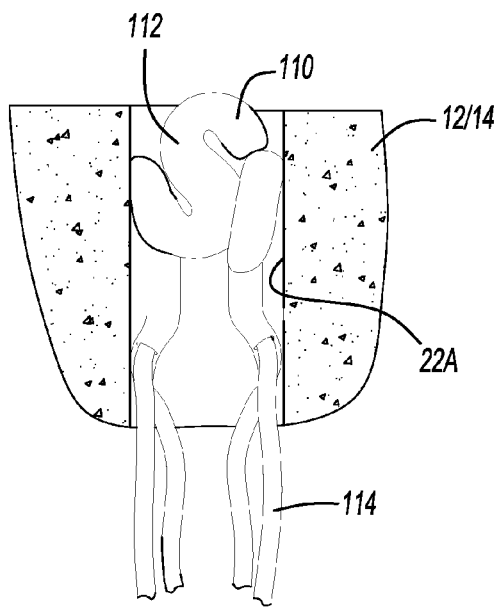
FIG. 5 illustrates another suture according to the present teachings, the suture anchored at an interior of a bone of the forearm.

With additional reference to FIG. 5, any one or more of the sutures 50 can be anchored at an interior of the radius 12 or the ulna 14 with an anchor 110. The anchor 110, which can be similar to the anchor 52 but collapsed to fit within the first bore 22A, expands to form an anchoring mass 112 upon tightening of suture strands 114 to thereby secure the anchor 110 to the radius 12 or ulna 14. The anchor 110 is similar to the anchor 150 of the suture construct 184 disclosed in U.S. application Ser. No. 12/915,962, the disclosure of which has been incorporated herein by reference. Additional description of the anchor 150 is thus included in U.S. application Ser. No. 12/915,962.

Figure 6:
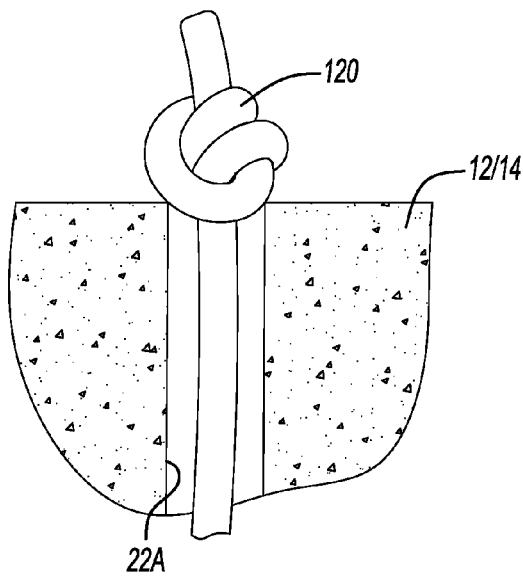
FIG. 6 illustrates an additional suture according to the present teachings, the suture anchored at an exterior of a bone of the forearm.

With reference to FIG. 6, any of the sutures 50, any of the other sutures described herein, and any of the sutures incorporated by reference can be secured to the radius 12 or the ulna 14 with a knot 120 having an outer diameter larger than the bore that the suture is seated within, such as the first bore 22A.

Figure 7:
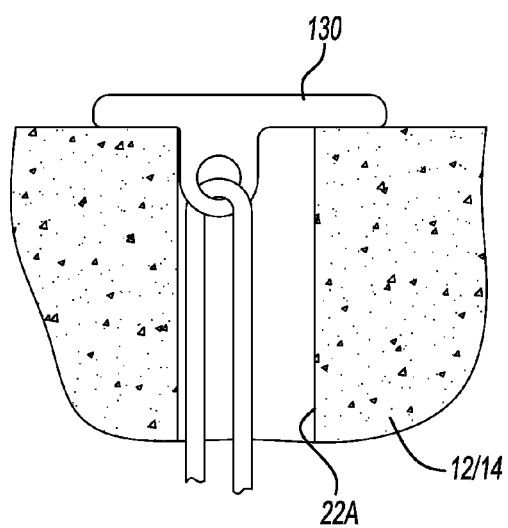
FIG. 7 illustrates yet another suture according to the present teachings, the suture anchored to an exterior of a bone of the forearm.

With reference to FIG. 7, any of the sutures 50, any of the other sutures described herein, and any of the sutures incorporated by reference can be secured to the radius 12 or the ulna 14 with a lever anchor 130 movable between a non-active position and an active position. In the non-active position, the lever anchor 130 is orientated such that is can pass through the bore that the suture is seated within, such as the first bore 22A. In the activated position, illustrated in FIG. 7, the lever anchor 130 extends across the bore at an exterior of the radius 12 or ulna 14 to secure the anchor 130 to the radius 12 or ulna 14. As an alternative to the illustrated anchor 130, any other suitable anchor member or button can be mounted to suture strands 14.

Figure 8:
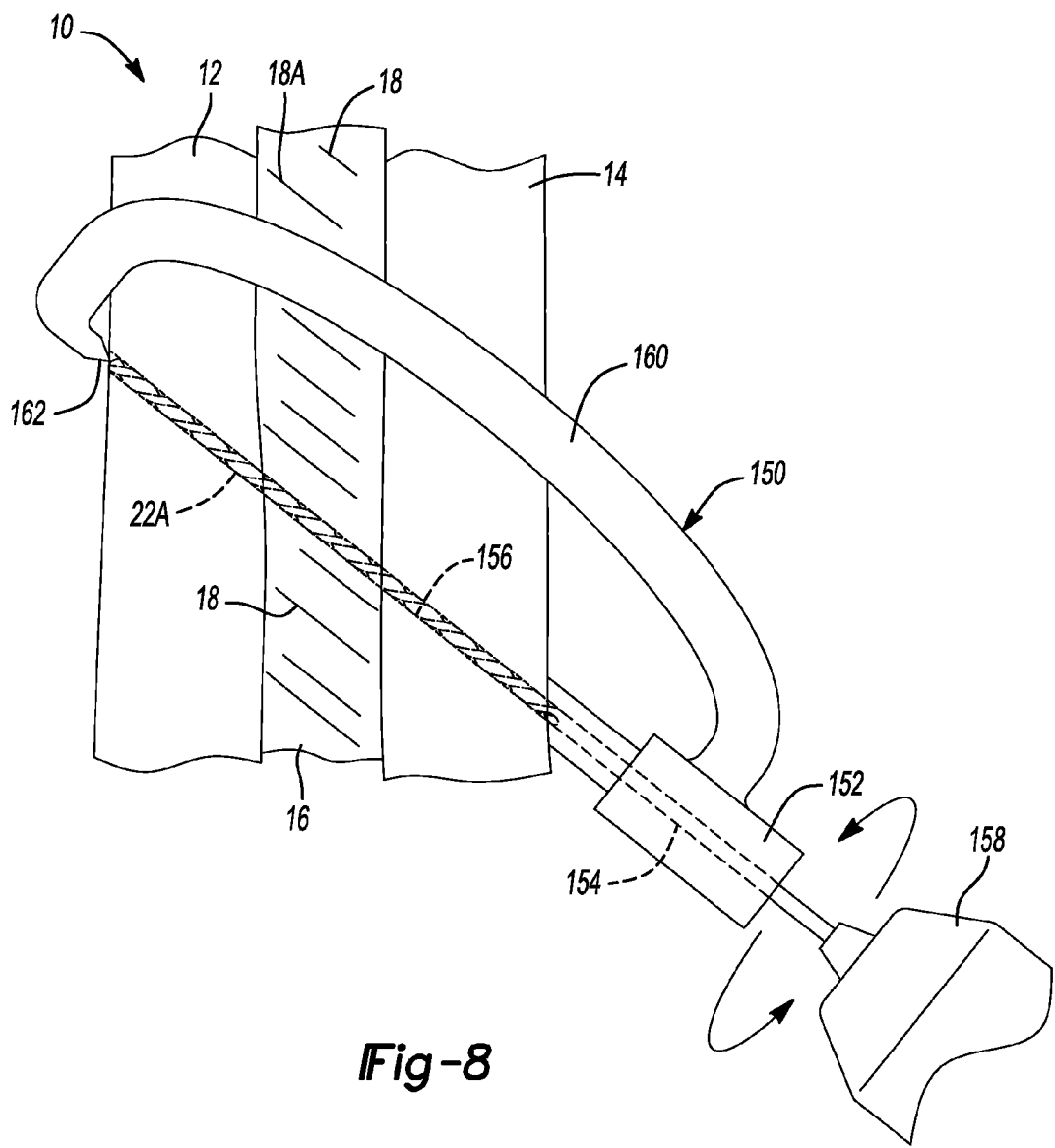
FIG. 8 illustrates a guide mounted to a forearm and preparation of the forearm to receive a suture.

With additional reference to FIG. 8, implantation of the suture 50A in the forearm 10 will be described. The first bore 22A can be drilled using any suitable guide, such as first drill guide 150. The first drill guide 150 generally includes a body 152 that defines a through hole 154 configured to receive a suitable cutting implement, such as drill bit 156 of a drill 158. Extending from the body 152 is a guide arm 160 sized and configured to span the forearm 10. At an end of the guide arm 160 opposite to the body 152 is a guide pin 162 that is suitable to engage an opposite side of the forearm 10 to assist in stabilizing the first drill guide 150 on the forearm 10.

The first drill guide 150 is orientated such that the through hole 154 is aligned parallel to the fibers 18 of the second group of interosseous fibers 18A. The drill 158 is positioned such that the drill bit 156 extends through the through hole 154 to engage the ulna 14. The drill 158 is then activated to drill the first bore 22A through the ulna 14, past the interosseous membrane 16, and through the radius 12. Drilling the first bore 22A past the interosseous membrane 16 can include through the interosseous membrane. The first drill guide 150 can be oriented in the opposite direction illustrated in FIG. 8, such that the body 152 abuts the radius 12 and the guide pin 162 abuts the ulna 14. The drill guide 150 can also be used to drill any of the other bores 22B-22E, as one skilled in the art will recognize.

Figure 9:
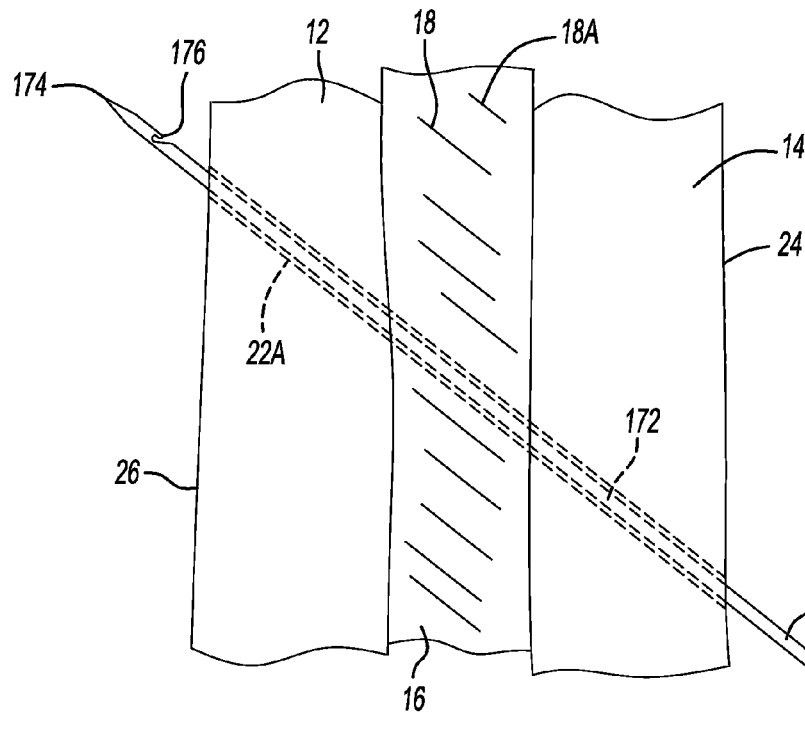
FIG. 9 illustrates an insertion pin extending through a bore formed in the forearm with the guide of FIG. 8.
Figure 10:
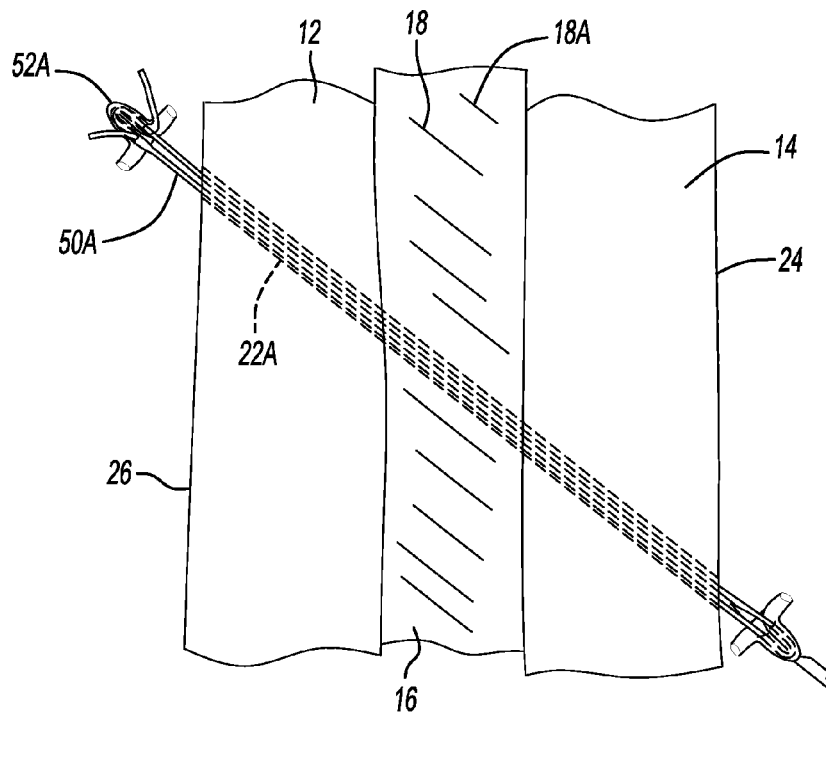
FIG. 10 illustrates the suture of FIG. 2 pulled through the bore formed in the forearm with the insertion pin.
Figure 11:
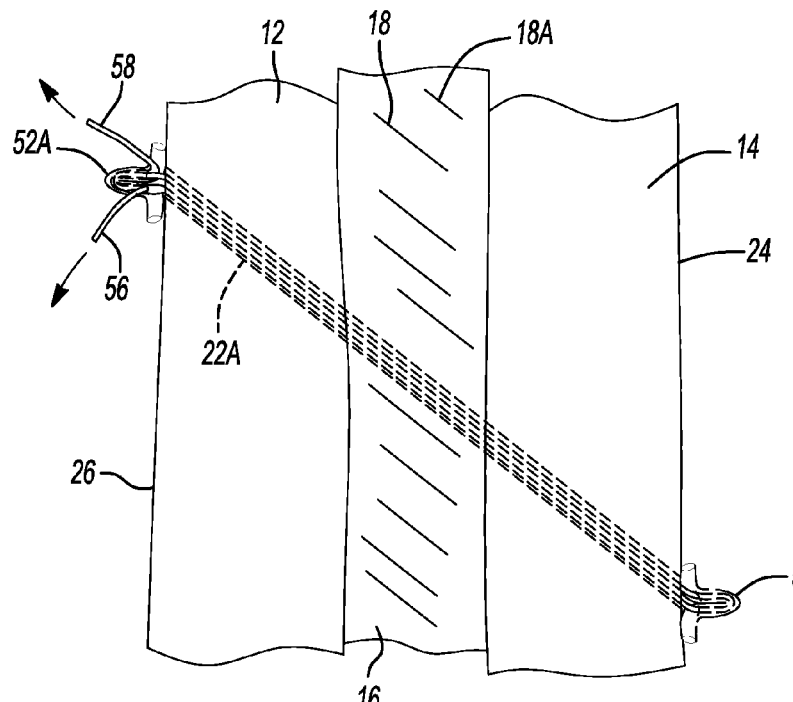
FIG. 11 illustrates the suture of FIG. 2 secured to the forearm according to the present teachings.

With additional reference to FIG. 9, a pin 170 can be used to guide the suture 50A through the first bore 22A and assist in initially stabilizing the radius 12 in relation to the ulna 14. The pin 170 includes an elongated shaft 172, a pointed distal end 174, and a hook 176 proximate to the distal end 174. The pin 170 is inserted through the first bore 22A such that the pointed distal end 174 and hook 176 of the pin 170 exit the forearm 10 through the radius 12. With additional reference to FIG. 10, the guide pin 162 hooks the suture 50A to pull the suture 50A into the first bore 22A. With the suture 50A seated within the first bore 22A such that the first anchor 52A is at an outer surface 26 of the radius 12 and the second anchor 52B is at the outer surface 24 of the ulna 14, the first end 56 and the second end 58 of the suture strand 54 are pulled to tighten and adjustably compress the first and second anchors 52A and 52B against the radius 12 and the ulna 14 respectively, as illustrated in FIG. 11.

Figure 12:
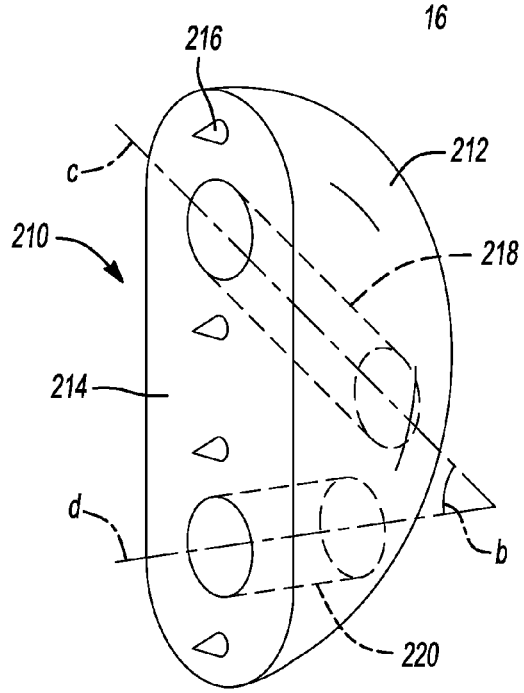
FIG. 12 is a perspective view of a drill guide according to the present teachings.

With additional reference to FIG. 12, a second drill guide is generally illustrated at reference numeral 210. The drill guide 210 includes a body 212 with a bone engaging surface 214. The bone engaging surface 214 is generally planar and includes a plurality of bone engagement teeth 216, which are pointed to facilitate secure engagement with either the radius 12 or the ulna 14. The second drill guide 210 defines a first through hole 218 and a second through hole 220. The first through hole 218 includes a first center axis C that is generally oblique to the bone engaging surface 214. The second through hole 220 includes a second center axis D that is generally perpendicular to a plane defined by the planar bone engaging surface 214. The first center axis C is orientated at an angle b, which is about 5° to about 55° relative to the second center axis D, such as about 20° to about 25° or about 40° to about 45°.

The angle b between the first center axis C and the second center axis D can be any suitable angle corresponding to the desired orientation of bores to be drilled in the forearm 10. For example, to drill the first bore 22E and the second bore 22E' as illustrated in FIG. 1B, the first through hole 218 will be angled from the second through hole 220 at an angle that corresponds to an angle at which the first bore 22E is to be angled from the second bore 22E', such as at an angle of from about 5° to about 55°, such as about 20° to about 25° or about 40° to about 45°. Thus, the second drill guide 210 can be used to form the first and second bores 22E and 22E' respectively for use in providing at least the following two different types of forearm stability: 1) stability along the longitudinal axis A provided by the second portion 50E" of the suture 50E extending through the second bore 22E' to prevent the radius 12 from moving relative to the ulna 14 perpendicular to the longitudinal axis A; and 2) load transfer stability, as well as natural range of motion during pronation and supination, provided by the first portion 50E' of the suture 50E extending through the first bore 22E.

Figure 13:
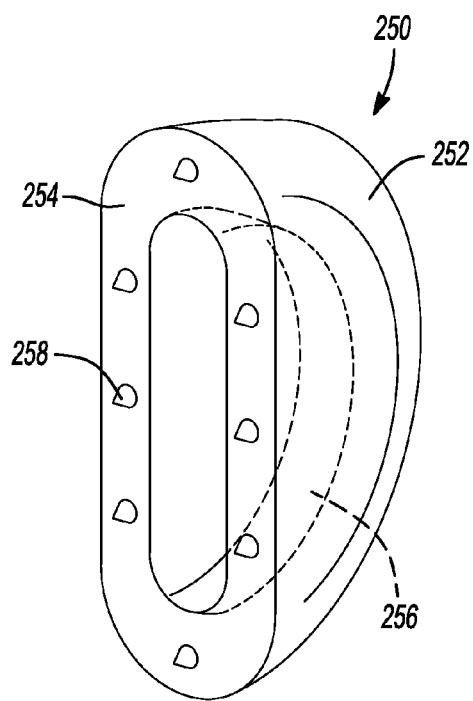
FIG. 13 is a perspective view of pin guide according to the present teachings.

With additional reference to FIG. 13, a pin guide is generally illustrated at reference numeral 250. The pin guide 250 generally includes a body 252 and a planar bone engaging surface 254. The body 252 generally defines a hemispherical guide surface 256. The planar bone engaging surface 254 includes a plurality of fixation members 258 that are sharpened and protrude from the bone engaging surface 254. The fixation members 258 can engage either the radius 12 or the ulna 14 to affix the pin guide 250 thereto.

Figure 14A:
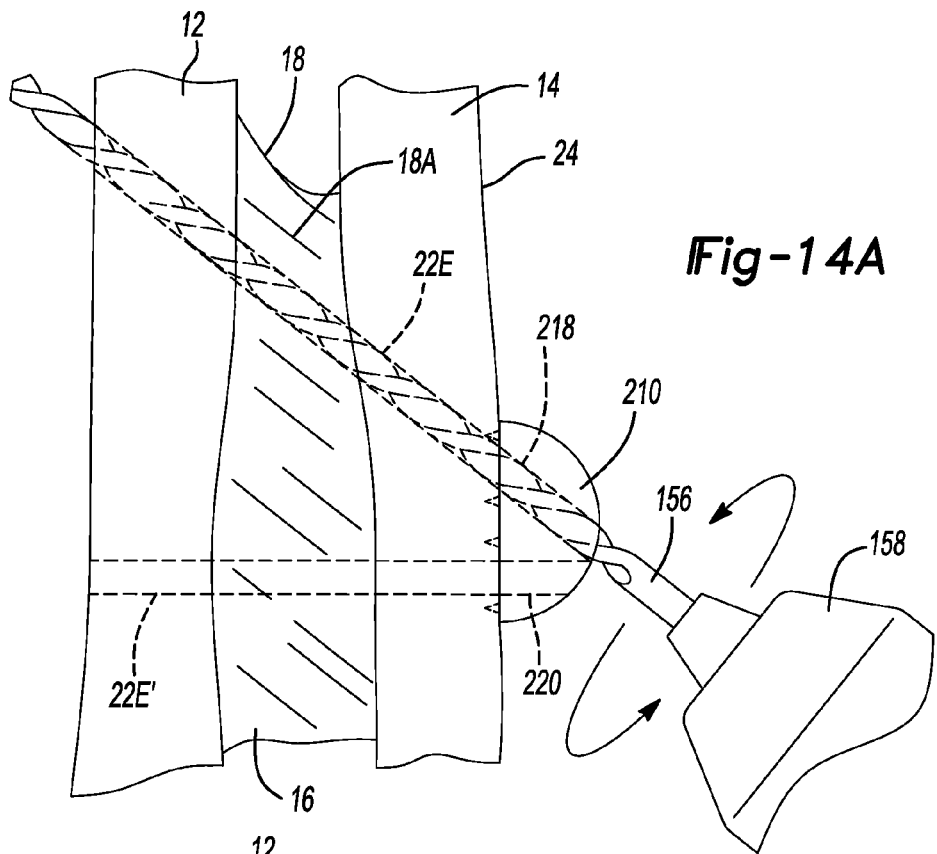
FIG. 14A illustrates the drill guide of FIG. 12 mounted to the forearm to guide a drill to form a first bore and a second bore in the forearm.
Figure 14B:
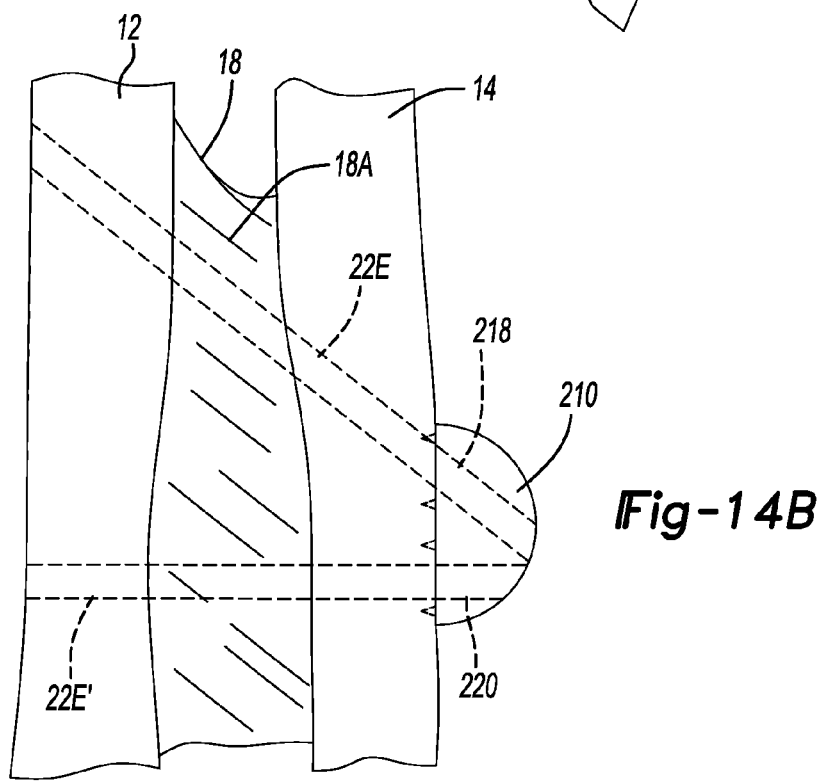
FIG. 14B illustrates first and second bores formed the forearm, the bores having been formed with the drill guided by the drill guide.

With additional reference to FIGS. 14A and 14B, the second drill guide 210 can be used to drill, for example, the first bore 22E and the second bore 22E' to receive the suture 50E. The second drill guide 210 is mounted to the outer surface 24 of the ulna 14 such that the bone engagement surface 214 contacts the outer surface 24 and the bone engagement teeth 216 are pressed into and through the outer surface 24. The drill bit 156 is inserted through the first through hole 218 and rotated by the drill 158 to form the first bore 22E. The drill bit 156 is inserted through the second through hole 220 and rotated by the drill 158 to form the second bore 22E'.

Figure 15:
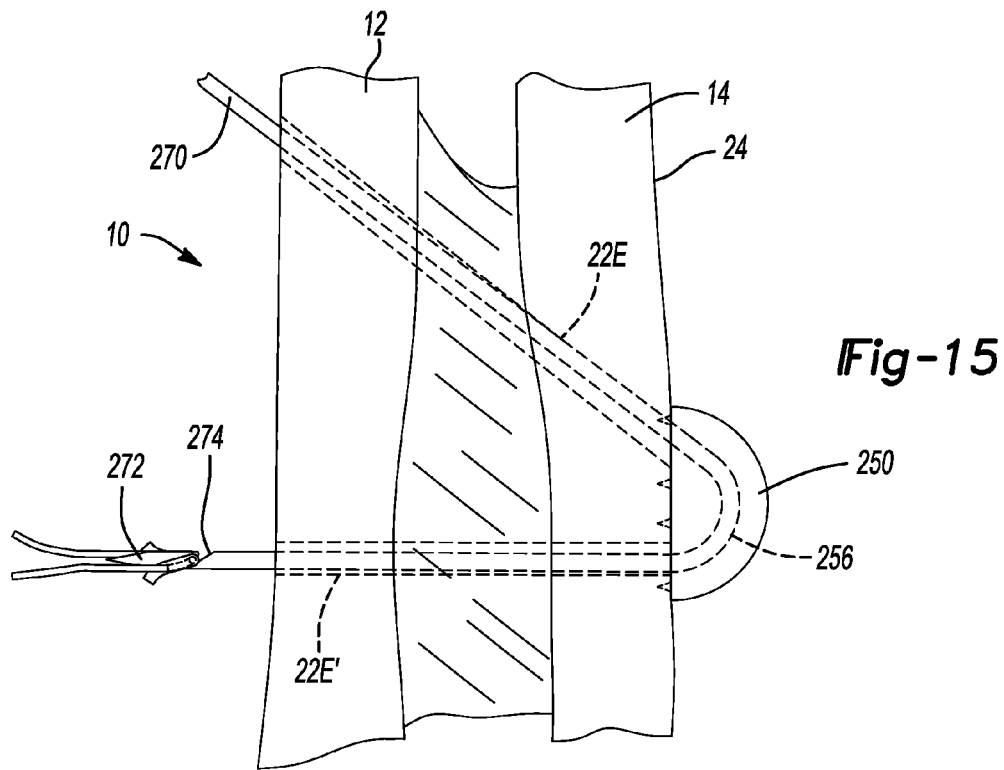
FIG. 15 illustrates the pin guide of FIG. 13 mounted to the forearm, the pin guide configured to guide a flexible guide pin through bores formed in the forearm using the drill guide.
Figure 16:
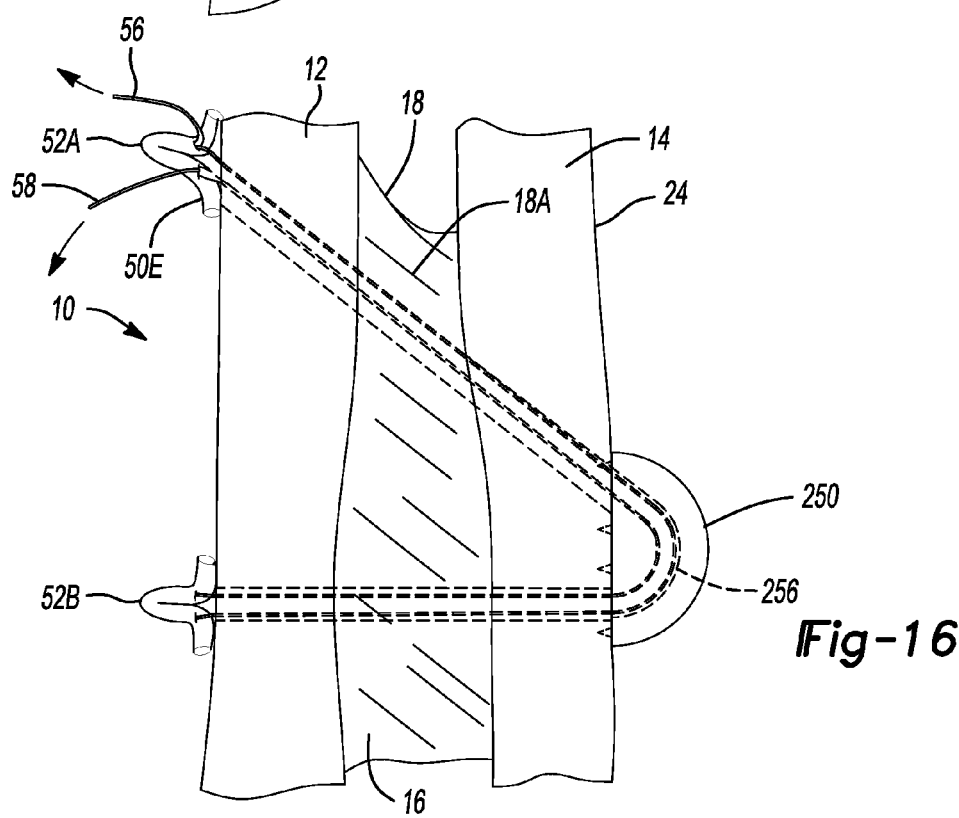
FIG. 16 illustrates the suture of FIG. 2 seated within the bores formed using the drill guide and fastened to the forearm.

With reference to FIGS. 15 and 16, after the first bore 22E and the second bore 22E' have been drilled, the pin guide 250 can be mounted to the outer surface 24 of the ulna 14 such that the pin guide 250 is aligned with the first bore 22E and the second bore 22E'. To position the suture 50E in the first and second bores 22E and 22E', a flexible guide pin 270 can be used, but is optional as one skilled in the art will recognize that the suture can be guided through the first and second bores 22E and 22E' in any suitable manner, such as without a guide. The flexible guide pin 270 includes a pointed distal end 272 and a hook 274 proximate to the pointed distal end 272. The flexible guide pin 270 is inserted into the first bore 22E at the radius 12 and pushed through the first bore 22E such that it reaches the pin guide 250. The pin guide 250 contacts the hemispherical guide surface 256, which directs the pointed distal end 272 of the flexible guide pin 270 into the second bore 22E'. As illustrated in FIG. 15, the flexible guide pin 270 then is pushed through the second bore 22E and exits the second bore 22E' at the outer surface 26 of the radius 12. The suture 50E is connected to the hook 274 and the flexible guide pin 270 is then pulled back through the second bore 22E' and the first bore 22E to position the suture 50E in both the first bore 22E and the second bore 22E', as illustrated in FIG. 16. With further reference to FIG. 16, the first end 56 and the second end 58 of the suture strand 54 are pulled to secure the suture 50E in the forearm 10. Rather than a single suture 50E extending through both the first bore 22E and the second bore 22E', separate sutures can be secured within each of the first bore 22E and the second bore 22E'.

Any two or more of the following can be provided in a kit: the first drill guide 150, the guide pin 170, the second drill guide 210, the pin guide 250, or flexible guide pin 270, each of which may be included in the kit in a plurality of different sizes and/or shapes. The kit may also include one or more of the sutures 50, as well as any of the other sutures described herein or incorporated by reference, or any other suitable fastening device.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system for repairing a defect in an interosseous membrane located between a first bone and a second bone, the system comprising:
    at least one suture;
    a drill guide including:
      a body;
      a bone engagement surface;
      a first through hole extending through the body, the first through hole defines a first drilling axis;
      a second through hole extending through the body, the second through hole defines a second drilling axis that is angled one of about 20° to 25° or about 40° to about 45° relative to the first drilling axis; and a pin guide defining a hemispherical guide surface.

2. The system of claim 1, further comprising a flexible guide pin configured to be guided by the pin guide.

3. The system of claim 2, wherein the flexible guide pin includes a pointed distal end and a hook proximate to the distal end configured to engage and guide the suture.

4. The system of claim 1, wherein the suture includes a self-locking, braided suture construct having a sleeve portion that defines a first opening and a second opening, a first end of the braided suture extends through both the first opening and the second opening, and a second end of the braided suture extends through both the first opening and the second opening.

5. The system of claim 4, wherein the braided suture construct further includes a first adjustable loop and a second adjustable loop, the first adjustable loop having a first deformable anchor attached thereon and the second adjustable loop having a second deformable anchor attached thereon.

6. The system of claim 4, wherein the braided suture construct includes a first deformable anchor and a second deformable anchor, the first deformable anchor is generally U-shaped and flexible and includes a base and a pair of feet, and the second deformable anchor is generally U-shaped and flexible and includes a base and a pair of feet.

7. The system of claim 1, wherein the pin guide includes a body having a bone engagement surface, wherein the body defines the hemispherical guide surface.

8. The system of claim 7, wherein the bone engagement surface of the pin guide includes a plurality of fixation members that protrude from the bone engaging surface and are configured to engage a bone.

9. A system for repairing a defect in an interosseous membrane located between a first bone and a second bone, the system comprising:
    a flexible guide pin;
    a drill guide including:
      a body;
      a bone engagement surface;
      a first through hole extending through the body, the first through hole defines a first drilling axis; and
      a second through hole extending through the body, the second through hole defines a second drilling axis that is angled relative to the first drilling axis; and
    a pin guide including:
      a body;
      a bone engagement surface; and
      a hemispherical guide surface defined within the body, wherein the hemispherical guide surface guides the flexible guide pin.

10. The system of claim 9, wherein the flexible guide pin includes a pointed distal end and a hook proximate to the distal end configured to engage and guide a suture.

11. The system of claim 9, wherein the bone engaging surface of the drill guide and the bone engagement surface of the pin guide each include a plurality of fixation members that protrude from the corresponding bone engaging surface and configured to engage a bone.

12. The system of claim 9, further comprising at least one suture wherein the suture includes a self-locking, braided suture construct having a sleeve portion with a first end of the braided suture and a second end of the braided suture extending through the sleeve portion to form first and second adjustable loops.

13. The system of claim 12, wherein the sleeve portion defines a first opening and a second opening and the first end of the braided suture extends through both the first opening and the second opening, and the second end of the braided suture extends through both the first opening and the second opening.

14. The system of claim 13, further comprising a first anchor associated with the first adjustable loop and a second anchor associated with the second adjustable loop.

15. The system of claim 14, wherein the first anchor and the second anchor are each flexible and each includes a base and a pair of feet.

16. A system for repairing a defect in an interosseous membrane located between a first bone and a second bone, the system comprising:
    at least one suture;
    a drill guide configured for guiding a drill through a bone;
    a flexible guide pin configured to carry the at least one suture;

a pin guide including:
  a body;
  a bone engagement surface; and
  a hemispherical guide surface defined by the body for guiding the flexible guide pin; and wherein the drill guide includes: a body; a bone engagement surface; a first through hole extending through the body, the first through hole defines a first drilling axis; and a second through hole extending through the body, the second through hole defining a second drilling axis that is angled relative to the first drilling axis.

17. The system of claim 16, wherein the drill guide includes:
  a body that defines a through hole configured to receive a drill bit;
  a guide arm sized and configured to span a forearm; and
  a guide pin extending from an end of the guide arm configured to engage an opposite side of the forearm to stabilize the drill guide on the forearm.

18. The system of claim 16, wherein the suture includes a self-locking, braided suture construct having a sleeve portion that defines a first opening and a second opening, a first end of the braided suture extends through both the first opening and the second opening, and a second end of the braided suture extends through both the first opening and the second opening.

* * * * *

UNITED STATES PATENT AND TRADEMARK OFFICE
CERTIFICATE OF CORRECTION

PATENT NO. : 9,445,827 B2  
APPLICATION NO. : 13/964558  
DATED : September 20, 2016  
INVENTOR(S) : Kaiser et al.

Page 1 of 1

It is certified that error appears in the above-identified patent and that said Letters Patent is hereby corrected as shown below:

On the Title Page

In item (54), and in the Specification, in Column 1, Line 2, in "Title", delete "INTRAOSSEOUS" and insert --INTEROSSEOUS--, therefor Signed and Sealed this
Thirteenth Day of March, 2018

Andrei Iancu
*Director of the United States Patent and Trademark Office*